US007354591B2

(12) United States Patent
Balloul et al.

(10) Patent No.: US 7,354,591 B2
(45) Date of Patent: *Apr. 8, 2008

(54) POXVIRUS WITH TARGETED INFECTION SPECIFICITY

(75) Inventors: Jean-Marc Balloul, Lingolsheim (FR); Stéphane Paul, Strasbourg (FR); Michel Geist, Lingolsheim (FR)

(73) Assignee: Transgene S.A., Strasbourg (FR)

( * ) Notice: Subject to any disclaimer, the term of this patent is extended or adjusted under 35 U.S.C. 154(b) by 1455 days.

This patent is subject to a terminal disclaimer.

(21) Appl. No.: 09/832,899

(22) Filed: Apr. 12, 2001

(65) Prior Publication Data
US 2003/0165477 A1 Sep. 4, 2003

Related U.S. Application Data

(60) Provisional application No. 60/256,080, filed on Dec. 15, 2000.

(30) Foreign Application Priority Data

Apr. 14, 2000 (EP) .................................. 00440109
Jan. 22, 2001 (EP) .................................. 01440009

(51) Int. Cl.
C12N 15/85 (2006.01)
(52) U.S. Cl. .................. 424/232.1; 435/5; 435/235.1
(58) Field of Classification Search ............... 424/93.1; 435/235.1
See application file for complete search history.

(56) References Cited

FOREIGN PATENT DOCUMENTS

WO    WO 92/06180 A1    4/1992
WO    WO 94/10323 A1    5/1994
WO    WO 94/27643 A1    12/1994

OTHER PUBLICATIONS

Paul. S. "Redirected cellular cytotoxicity by infection of effector cells with a recombinant vaccinia virus encoding a tumor-specific monoclonal antibody" 2000 Cancer Gene Ther. (2000) 7, pp. 615-623.*
Hsiao. J.C. "Cell Surface Proteoglycans Are Necessary for A27L Protein-Mediated Cell Fusion: Identification of the N-tmerinal Region of A27L Protein as the Glycoaminoglycan-Binding Domain" Journ. of Virol. (Oct. 1998) 72, pp. 8374-8379.*
Gomez, C.E. "Recombinant proteins produced by vaccinia virus vectors can be incorporated within the vriou (IMV form) into different compartments" Arch. Virol. (2001) vol. 146, pp. 875-892.*
Haisman et al. "Targeting of adenoviral vectors through a bispecific single-chain antibody" Cancer Gene Therapy (2000) 7, 6, 901-904.*
Collado et al. Chimeras between the human immunodeficiency virus (HIV-1) Env and vaccinia virus immunogenic proteins p14 and p39 generate in mice broadly reactive antibodies and specific activation of CD8+ T cell responses Vaccine (Jul. 2000) 18, 3123-313.*
Janeway et al. Immunobiology. (1999) Elsevier Science Ltd/Garland Publishing. p. 187, 278, 291.*
Balloul et al. Cell. Molecular Biology 1994, vol. 40, p. 49-59.*
Vazquez et al. J. Virology, 1998, vol. 72, p. 1-23.*
Chung et al. (Journal of Virology, 1998, vol. 72, p. 1577-1585).*
Schumacher et al. (The Journal of Histochemistry and Cytochemistry, 1998,vol. 46, p. 127-134).*
European Search Report for EP/01 40 09432 dated Jul. 26, 2001, 3 pages.
Galmiche et al., "Expression of a functional single chain antibody on the surface . . . tumour cell targeting", Journal of General Virology, 1997, pp. 3019-3027, vol. 78, Great Britain.
Russel et al., "Retroviral vectors displaying functional antibodu fragments", Oxford University Press, 1993, pp. 1081-1085, vol. 21, No. 5, United Kingdom.
Bernard Moss, "Genetically engineered poxviruses for recombinant gene expression, vaccination, and safety", Colloquium Paper, 1996, pp. 11341-11348, vol. 93, USA.
Kianmanesh et al., "A "Distant" Bystander Effect of Suicide Gene Therapy: Regression of Nontransduced Tumors Together with a Distant Transduced Tumor", *Human Gene Therapy*, Oct. 10, 1997, 8:1807-1814, Mary Ann Liebert, Inc., Larchmont, New York.
Adachi et al., "Experimental Gene Therapy for Brain Tumors Using Adenovirus-Mediated Transfer of Cytosine Deaminase Gene and Uracil Phosphoribosyltransferase Gene with 5-Fluorocytosine", *Human Gene Therapy*, Jan. 1, 2000, 11:77-89, Mary Ann Liebert, Inc., Larchmont, New York.
Miller et al., "Targeted Vectors for Gene Therapy" The FASEB Journal, vol. 9, Feb. 1995, pp. 190-199.
Bakker et al., "A Tropism-Modified Adenoviral Vector Increased the Effectiveness of Gene Therapy for Arthritis", Gene Therapy, 2001: 8, 1785-1793.
Nettelbeck et al., "Targeting of Adenovirus to Endothelial Cells by a Bispecific Single-Chain Diabody Directed Against the Adenovirus Fiber Knob Domain and Human Endoglin (CD105)" Molecular Therapy, vol. 3, No. 6, Jun. 2001.

* cited by examiner

*Primary Examiner*—Bruce Campell
*Assistant Examiner*—Agnieszka Boesen
(74) *Attorney, Agent, or Firm*—Buchanan, Ingersoll & Rooney, PC

(57) ABSTRACT

The present invention concerns a poxviral particle having a targeted infection specificity conferred by an heterologous ligand moiety present at the surface of said poxviral particle and capable of specifically recognizing and binding to an anti-ligand molecule localized at the surface of target cells. The present invention further relates to a vector comprising a nucleotide sequence encoding a chimeric polypeptide including such an heterologous ligand moiety and all or part of a natural poxviral surface polypeptide. The present invention additionally concerns compositions comprising said poxviral particle or said vector as well as their use for therapeutic and prophylactic purposes. The invention is of very special interest in gene therapy applications, in particular in preventing or treating cancer in mammals.

14 Claims, 3 Drawing Sheets

SEQUENCE LISTING

<160> NUMBER OF SEQ ID NOS: 21

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:PCR primer
    to amplify the MVA 138L gene and flanking region

<400> SEQUENCE: 1
cagactggac ggcgtccata tgag                                              24

<210> SEQ ID NO 2
<211> LENGTH: 61
<212> TYPE: DNA
<213> ORGANISM: Artificial Sequence
<220> FEATURE:
<221> NAME/KEY: gene
<222> LOCATION: Complement((1)..(61))
<223> OTHER INFORMATION: Description of Artificial Sequence: antisens
      PCR primer to amplify the 3' end of MVA 138L gene and
      3' flanking region

<400> SEQUENCE: 2 catttttaa gtatagaata aaagatcccg ggagtaccat cgtgattctt accagatatt        60
a                                                                       61

<210> SEQ ID NO 3
<211> LENGTH: 61
<212> TYPE: DNA
<213> ORGANISM: Artificial Sequence
<220> FEATURE:
<223> OTHER INFORMATION: Description of Artificial Sequence: PCR primer
      to amplify E. coli gpt gene and H5R promoter
<221> NAME/KEY: gene
<222> LOCATION: (1)..(61)

<400> SEQUENCE: 3
taatatctgg taagaatcac gatggtactc ccgggatctt ttattctata cttaaaaat        60 g                                                                       61

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: antisense
      PCR primer to amplify E. coli GPT gene and pH5R
      promoter

<400> SEQUENCE: 4
ggggttaatt aaggaagtta aaaagaacaa cgccc                                  35

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: PCR
      primer to amplify the upstream region of MVA 138L gene.

<400> SEQUENCE: 5
gggggaattc gagcttatag cgtttagttc aggtacgg                               38

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence:
      antisense PCR primer to amplify the upstream region of the MVA
      138L gene

<400> SEQUENCE: 6
ggggaagctt ttaaagtaca gattttagaa actgacactc tgcg    44

<210> SEQ ID NO 7
<211> LENGTH: 68
<212> TYPE: DNA
<213> ORGANISM: Artificial Sequence
<220> FEATURE:
<223> OTHER INFORMATION: Description of Artificial Sequence:antisense
      primer to amplify the upstream region of the MVA
      138L gene

<400> SEQUENCE: 7
ggggaagctt caagagcggc acggctcccg ccgctgcgac gttcaggagg accaaggcaa    60
ccacgaac    68

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: PCR
      primer to amplify the MVA 138L gene and its downstream
      region

<400> SEQUENCE: 8
ggggaagctt atggacggaa ctcttttccc c    31

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence:
      antisense PCR primer to amplify the MVA 138L gene and its
      downstream region

<400> SEQUENCE: 9
gggggaattc gcttatcgtt atcgggttta gcttctg    37

<210> SEQ ID NO 10
<211> LENGTH: 68
<212> TYPE: DNA
<213> ORGANISM: Artificial Sequence
<220> FEATURE:
<223> OTHER INFORMATION: Description of Artificial Sequence: PCR
      primer to amplify SM3 scFv sequence

<400> SEQUENCE: 10
cgcagagtgt cagtttctaa aatctgtact ttaaatggtg cagctgcagg agtctggagg    60
aggcttgg    68

<210> SEQ ID NO 11
<211> LENGTH: 58
<212> TYPE: DNA
<213> ORGANISM: Artificial Sequence
<220> FEATURE:
<223> OTHER INFORMATION: Description of Artificial Sequence: antisense
      PCR primer to amplify the SM3 scFv sequence

<400> SEQUENCE: 11
gatcgtcatc tccggggaaa agagttccgt ccatcagttt ggttcctcca ccgaacac    58

<210> SEQ ID NO 12
<211> LENGTH: 57
<212> TYPE: DNA
<213> ORGANISM: Artificial Sequence

```
<220> FEATURE:
<223> OTHER INFORMATION: Description of Artificial Sequence: PCR
      primer to amplify the SM3 scFv sequence

<400> SEQUENCE: 12
cctgaacgtc gcagcggcgg gagccgtgcc gctcttggtg cagctgcagg agtctgg      57

<210> SEQ ID NO 13
<211> LENGTH: 111
<212> TYPE: DNA
<213> ORGANISM: Artificial Sequence
<220> FEATURE:
<223> OTHER INFORMATION: Description of Artificial Sequence: sequence
      of the synthetic p11k7.5 promoter

<400> SEQUENCE: 13
ataaaaatat agtagaattt catttgtttt tttctatgct ataaatagga tccgataaag    60
tgaaaaataa ttctaattta ttgcacggta aggaagtaga atcataaga a              111

<210> SEQ ID NO 14
<211> LENGTH: 53
<212> TYPE: DNA
<213> ORGANISM: Artificial Sequence
<220> FEATURE:
<223> OTHER INFORMATION: Description of Artificial Sequence:PCR primer
      to amplify the p11k7.5 promoter

<400> SEQUENCE: 14
gggggatccc ccgggctgca gaagcttttc tttatgattc tacttcctta ccg           53

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: antisense
      PCR primer to amplify the p11k7.5 promoter

<400> SEQUENCE: 15 gggggggagat ctaagcttgt cgacataaaa atatagtaga atttcatttg              50

<210> SEQ ID NO 16
<211> LENGTH: 77
<212> TYPE: DNA
<213> ORGANISM: Artificial Sequence
<220> FEATURE:
<223> OTHER INFORMATION: Description of Artificial Sequence: synthetic
      sequence

<400> SEQUENCE: 16
gatggtgaca gggggaatgg caagcaagtg ggatctcgag ttgggtgact tggtgacag    60 atactactgt gtttaag                                                   77

<210> SEQ ID NO 17
<211> LENGTH: 85
<212> TYPE: DNA
<213> ORGANISM: Artificial Sequence
<220> FEATURE:
<223> OTHER INFORMATION: Description of Artificial Sequence: synthetic
      sequence

<400> SEQUENCE: 17
gatccttaaa cacagtagta tctgtcacca aagtcaccca actcgagatc ccacttgctt    60
gccattcccc ctgtcaccat ctgca                                          85
```

```
<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence:PCR primer
      to amplify the 5' F13L flanking region of MVA

<400> SEQUENCE: 18
gagaggatcc gggtatctag ccacagtaaa tc                                32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence:
      Description of Artificial Sequence :antisense PCR primer to
      amplify the 5' F13L flanking region of MVA

<400> SEQUENCE: 19
tttcgaattc ggaatctgta ttctcaatac cg                                32

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: PCR
      primer to amplify the 3' F13L flanking region of MVA

<400> SEQUENCE: 20
atctgaattc gtggagatga tgatagttta agc                               33

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence:
      antisense PCR primer to amplify the 3' F13L flanking region of
      MVA

<400> SEQUENCE: 21
aacaggatcc cttatacatc ctgttctatc aacg                              34
```

POXVIRUS WITH TARGETED INFECTION SPECIFICITY

This application claims priority under 35 U.S.C. §§ 119 and/or 365 to EP 00440109.7 filed in Europe on Apr. 14, 2000; EP 01440009.7 filed in Europe on Jan. 22, 2001; and 60/256,080 filed in U.S. on Dec. 15, 2000 the entire content of which is hereby incorporated by reference.

The present invention concerns a poxviral particle having a targeted infection specificity conferred by an heterologous ligand moiety present at the surface of said poxviral particle and capable of specifically recognizing and binding to an anti-ligand molecule localized at the surface of target cells. The present invention further relates to a vector comprising a nucleotide sequence encoding a chimeric polypeptide including such an heterologous ligand moiety and all or part of a natural poxviral surface polypeptide. The present invention additionally concerns compositions comprising said poxviral particle or said vector as well as their use for therapeutic and prophylactic purposes. The invention is of very special interest in gene therapy applications, in particular in preventing or treating cancer in mammals.

Gene therapy can be defined as the transfer of genetic material into a cell or an organism. The possibility of treating human disorders by gene therapy has changed in few years from the stage of theoretical considerations to that of clinical applications. The first protocol applied to man was initiated in the USA in September 1990 on a patient suffering from adenine deaminase (ADA) deficiency. This first encouraging experiment has been followed by numerous new applications and promising clinical trials based on gene therapy are currently ongoing.

Successful gene therapy depends principally on the efficient delivery of a therapeutic gene of interest to make its expression possible into cells of a living organism. Therapeutic genes can be transferred into cells using a wide variety of vectors resulting in either transient expression (transfection) or permanent transformation of the host genome. During the past decade, a large number of viral, as well as non-viral, vectors has been developed for gene transfer (see for example Robbins et al., 1998, Tibtech 16, 35-40 and Rolland, 1998, Therapeutic Drug Carrier Systems 15, 143-198 for reviews).

The most widely used viral vectors are derived from retroviruses and adenoviruses (for review, see Miller, 1997, Human Gene Therapy 8, 803-815). However, other viral vectors such as Sindbis virus-derived vectors or poxvirus-derived vectors, are emerging as promising candidates for in vivo gene transfer.

Poxviruses are a group of complex enveloped viruses that distinguish them principally by their unusual morphology, their large DNA genome and their cytoplasmic site of replication. The genome of several members of poxviridae, including the Copenhagen vaccinia virus (VV) strain (Goebel et al., 1990, Virol. 179, 247-266 and 517-563; Johnson et al., 1993, Virol. 196, 381-401) and the modified vaccinia virus Ankara (MVA) strain (Antoine et al., 1998, Virol. 244, 365-396), have been mapped and sequenced. VV has a double-stranded DNA genome of about 192 kb coding for about 200 proteins of which approximately 100 are involved in virus assembly. MVA is a highly attenuated vaccinia virus strain generated by more than 500 serial passages of the Ankara strain of vaccinia virus (CVA) on chicken embryo fibroblasts (Mayr et al., 1975, Infection 3, 6-16). The MVA virus was deposited before Collection Nationale de Cultures de Microorganismes (CNCM) under depositary N° I-721. Determination of the complete sequence of the MVA genome and comparison with the Copenhagen VV genome allows the precise identification of the alterations which occurred in the viral genome and the definition of seven deletions (I to VII) and numerous mutations leading to fragmented ORFs (Open Reading Frame) (Antoine et al., 1998, Virology 244, 365-396).

The natural pathway for intracellular uptake of enveloped viruses involves a series of steps including the binding of a viral polypeptide exposed at the virus surface to a cellular receptor and a fusion mechanism between the viral and cellular membranes resulting in viral genome release into the cytoplasm of the infected cell.

However, in poxvirus special case, the exact delivery pathway analysis is complicated by the existence of two morphologically distinct forms of infectious virus, termed intracellular mature virus (IMV) and extracellular enveloped virus (EEV). The IMV form is, among other particularities, characterized by a monolipid envelope surrounding the viral core (FIG. 1) and is principally localized in the cytoplasm of the infected cells, although it might be extracellularly released after lysis of the infected cells. Many of the natural polypeptides exposed at the surface of the IMV lipid envelope have been identified, such as for example the p14 kDa and p21 kDa proteins, respectively encoded by the A27L gene (Rodriguez at al., 1985, J. Virol. 56, 482-488; Rodriguez et Estaban, 1987, J. Virol. 61, 3550-3554) and the A17L gene, as well as proteins encoded by L1R, A14L, D8L, A9L (Yeh et al., 2000, J. Virol. 74, 9701-9711), E10R (Senkevich et al., 2000, Virol. 5, 244-252) and H3L genes. Compared to the IMV, the EEV form has an additional outer lipid membrane envelope (double lipid layer) acquired from the trans-Golgi network cisternae. It corresponds to the viral form released outside the infected cells. The EEV surface membrane envelope shows about 10 proteins which are absent from the IMV surface, such as for example the encoded B5R, A34R and hemagglutinin (HA) gene products (FIG. 1). The co-existence of said IMV and EEV forms has been described for most of the vaccinia strains (e.g. Copenhagen and MVA strains) as well as for other poxviruses such as the fowl poxvirus (Boulanger et al., 2000, J. Gen. Virol. 81, 675-687).

The different morphologies of IMV and EEV suggest the occurrence of different mechanisms for the penetration of these poxviral forms into the host cells. It has been recently proposed that the EEV delivery pathway is mediated by endocytosis and subsequent pH-dependent membrane fusion pathway, whereas the IMV form fuses directly with the cellular membrane in a pH-independent manner (Vanderplasschen et al., 1998, J. Gen. Virol. 79, 877-887). Two cellular receptors that mediate IMV binding and intracellular uptake have been recently identified: the heparan sulfate which is a glycosaminoglycan (GAG) side chain of cell surface proteoglycans (Chung et al., 1998, J. Virol. 72, 1577-1585) and another GAG component, the chondroitin sulfate (Hsiao et al., 1999, J. Virol. 73, 8750-8761). Both receptor interacts with a different IMV surface polypeptide, respectively the p14 (binding with heparan sulfate) and D8L gene product (binding with chondroitin sulfate), suggesting different type of virus-GAG interactions.

The vaccinia virus 14-kDa protein (p14) plays an important role in the infectious property of the virus. The p14 protein is anchored in the IMV lipid envelope by association with the 21-kDa protein (p21). The p14 protein is involved in the IMV delivery pathway, probably by participating to the attachment to the cell-surface heparan sulfate (Chung et al., 1998, J. Virol. 72, 1577-1585). In addition, the fusion process has been attributed to said p14 protein. Furthermore, as a general statement, it has been shown that the IMV surface polypeptides are closely related to IMV infectious property and that their mutation or deletion dramatically impaired IMV dissemination (Dallo et al., 1987,Virology 159, 423-32). The p14 protein is also necessary for EEV formation and virus spread outside the infected cells. Recently, the functional domains required for binding to cell surface heparan sulfate receptor, for virus/cell membrane fusion and virus release have been mapped within the 43 first N-terminal amino acids of the p14 (Vazquez and Esteban, 1999, J. Virol. 73, 9098-9109). Besides, Vazquez et al. (1998, J. Virol. 72, 10126-10137) have shown that the C-terminal domain of the p14 is involved in the binding with the p21 protein.

Many recombinant poxviral vectors expressing various therapeutic genes have been reported in the literature. In particular, VV expressing cytokine genes (Peplinski et al., 1995, Ann. Surg. Oncol. 2, 151-159; Whitman et al., 1994, Surgery 116, 183-188), B7.1 immunostimulatory gene (Hodge et al., 1994, Cancer Res. 54, 5552-5555), ICAM-1 (Uzendoski et al., 1997, Hum. Gene Ther. 8, 851-860) or suicide genes such as the thymidine kinase gene of herpes simplex virus-1 (TK HSV-1) (Puhlmann et al., 1999, Hum. Gene Ther. 10, 649-657) and the cytosine deaminase gene (Gnant et al., 1999, Cancer Res. 59, 3396-3403) have been proposed for cancer therapy. In addition, their anti-tumoral activity has been demonstrated in animal models. Vectors based on MVA strain have also been proposed (Sutter and Moss, 1992, Proc. Natl. Acad. Sci. USA 89, 10847-10851; Carroll and Moss, 1995, BioTechniques 19, 352-355; Antoine et al., 1996, Gene 177, 43-46; Schleiflinger et al., 1996, Arch. Virol. 141, 663-669).

However, vaccinia virus displays a very broad host range and can infect most vertebrates cells. Again, it should be noted that the IMV and EEV forms differ with respect to this disseminating property because the EEV presenting onto its surface a larger variety of polypeptides than onto the IMV surface, it is more prone to disseminate widely than IMV. Although, whatever form is considered, this absence of infection selectivity could be regarded as a disadvantage for special applications where it is desirable to limit adverse effects that could result from the expression of transferred genes (i.e. cytotoxic genes) in the non-target cells. Accordingly, it would be interesting to modify the virus in order to restrict its host range to direct the infection to target cell populations.

The modification of viral tropism has already been achieved with certain viruses. For example in WO931/09221, influenza virus tropism is modified by inhibition of the viral hemagglutinin polypeptide which normally mediates the binding of the virus to the cellular receptor by means of a monoclonal antibody and by coupling the virus with an antibody capable of interacting with the transferrin receptor expressed onto targeted cells.

Roux et al. (1989, Proc. Natl. Acad Sci. USA 86, 9079-9083) reports the infection of human cells with a mouse ecotropic recombinant retrovirus using two biotinylated antibodies directed to the retroviral envelope gp70 and to a cellular antigen of the human major histocompatibility complex (MHC), respectively.

WO94/10323 describes targeted adenoviruses vectors exhibiting at their surface a fiber protein modified by fusion with a single chain antibody, in order to direct adenoviral infection to the cells expressing the antibody-recognized antigen.

However, controlled targeting of poxviral particles has been hampered by the intrinsic complexity of the poxviruses and the existence of the two different infectious forms. In this regard, Galmiche et al. (1997, J. Gen. Virol. 78, 3019-3027) reports the construction of EEV particles for tumor cells targeting. A single chain antibody directed against the tumour-associated antigen ErbB-2 was fused to the viral hemagglutinin (HA) in order to be expressed at the EEV surface. ErbB-2 is an epidermal growth factor receptor that is over-expressed onto human adenocarcinoma cells. Although the fusion protein is exposed at the surface of the EEV particle and is able to bind cultured human adenocarcinoma cells in vitro, the authors did not observe preferential infection towards ErbB-2 expressing cells of the EEV having the antibody-HA fusion. It is presumed that the modified EEV particle still contains yet unidentified protein(s) allowing infection of a broad range of cells.

Therefore, the technical problem underlying the present invention is the provision of improved methods and means for the targeting of poxviral particles to specific cells. This technical problem is solved by the provision of the embodiments as defined hereby.

The present invention concerns a poxviral particle having a targeted infection specificity towards target cells wherein said particle infects preferably said target cells and wherein said specificity is conferred by at least one heterologous ligand moiety which is localized at the surface of said poxviral particle and which is capable of binding an anti-ligand molecule localized at the surface of said target cells, with the proviso that when said poxviral particle is an EEV vaccinia virus particle said ligand is not an antibody directed to ErbB-2.

The term "a targeted infection specificity (of a poxviral particle) towards target cells" as used herein refers to a controlled infection specificity, where a poxviral particle of the present invention is engineered to display a new or enhanced tropism towards said target cells, compared to a related non modified (i.e. wild type) poxvirus particle. As a result, the poxviral particle of the present invention shows a propensity to infect said target cells unlike its related non modified poxviral particle, which means that the poxviral particle of the present invention infects more efficiently or more rapidly its target cells (displaying at their surface the anti-ligand recognized by the ligand moiety displayed at the surface of the poxviral particle of the invention) than non target cells (that do not display at their surface such an anti-ligand), whereas a related non modified poxviral particle will infect said target cells with a lower or a similar efficiency compared to non-target cells. This preferred infectious property can be easily determined by comparing the infection property of the poxviral particle of the present invention with infection property of its related non modified poxviral particle towards target cells and non target cells, either in vitro (e.g. in cultured cells) or in vivo (e.g. in animal models) and under the same experimental conditions. In vitro experimental conditions for analyzing infection properties are provided in Example 5 of the present specification, however other methods are well known by those skilled in the art and are thus usable in the context of the invention. For example, when a mixture of poxviral particles according to the invention and of related non modified poxviral particles are used to infect cultured target cells with relatively short infection time (lower than 30 min and especially 1 to 10 min), a majority (at least 60%, preferably, at least 70% and more preferably, at least 80%) of the poxviral particles according to the invention comprised in the original mixture are able to infect said target cells, whereas a minority (at most 40%, preferably, at most 30% and more preferably, at most 20%) of the related non modified poxviral particles comprised in the original mixture are able to infect said target cells. This results in an enrichment of the quantity of poxviral particles according to the invention present in the mixture at each infection round. Such an enrichment can be evaluated by determining the viral titers of the respective poxviral particles by standard techniques.

The term "ligand moiety" as used in the present invention defines any moiety capable of recognizing and binding to at least one anti-ligand molecule that is expressed or exposed at the surface of a target cell. It provides the target cell binding and infection specificity to the poxviral particle of the invention. It is evident by reading the specification that said anti-ligand molecule is different from the natural cellular receptor mediating poxvirus uptake (e.g. heparan sulfate or chondroitin sulfate). According to the invention, the ligand moiety is localized on the surface of the claimed poxviral particle. Depending on the used coupling method (see below), said ligand moiety may be a moiety added to and exposed on the viral particle surface (for example by chemical coupling) or a moiety fused in the particle envelope structure (for example by genetic coupling). "Heterologous" means that said ligand moiety is not found at the surface of a wild type poxviral particle. By extension, "homologous" refers to the polypeptides or natural moieties found at the surface of a wild type poxviral particle. The anti-ligand molecule localized at the surface of a target cell is preferably one that the wild type poxviral particle does not bind or one that the wild type poxviral particle binds but with a lower specificity than a modified poxviral particle of the present invention. The binding specificity between a ligand and a given anti-ligand molecule can be determined according to techniques of the art, including ELISA, immunofluorescence and surface plasmon resonance-based technology (Biacore AB).

In general, the ligand moieties that may be used in the context of the present invention are widely described in the literature; it is a moiety able to confer to the modified poxviral particle of the invention, the ability to bind to a given anti-ligand molecule or a class of anti-ligand molecules localized at the surface of at least one target cell. Suitable anti-ligand molecules include without limitation polypeptides selected from the group consisting of cell-specific markers, tissue-specific markers, cellular receptors, viral antigens, antigenic epitopes and tumor-associated markers. Anti-ligand molecules may moreover consist in sugar, lipid, glycolipid, antibody, etc. . . . According to the invention, a ligand moiety may be for example a lipid, a glycolipid, an hormone, a sugar, a polymer (e.g. PEG, polylysine, PEI, . . . ), a polypeptide, an oligonucleotide, a vitamin, an antigen, a lectin, a polypeptide moiety presenting targeting property such as for example JTS1 (WO 94/40958), an antibody or combination thereof. A fragment of the precited ligand moiety can also be employed provided that it retains the targeting property of the natural molecule.

Preferably, the ligand moiety used in the present invention is a polypeptide having a minimal length of 7 amino acids. It is either a native polypeptide or a polypeptide derived from a native polypeptide. "Derived" means containing (i) one or more modifications with respect to the native sequence (e.g. addition, deletion and/or substitution of one or more residues), (ii) amino acid analogs, including not naturally occurring amino acids or (iii) substituted linkages as well as (vi) other modifications known in the art. This term encompasses variant and chimeric polypeptides obtained by fusing sequences of various origins. In addition, the ligand moiety may have a linear or cyclized structure (e.g. by flanking at both extremities a polypeptide ligand by cysteine residues). Additionally, the ligand moiety in use in the invention may include modifications of its original structure by way of substitution or addition of chemical moieties (e.g. glycosylation, alkylation, acetylation, amidation, phosphorylation, addition of sulfhydryl groups and the like). The invention further contemplates modifications that render the ligand moiety detectable. For this purpose, modifications with a detectable moiety can be envisaged (i.e. a scintigraphic, radioactive, fluorescent, or dye labels and the like). Suitable radioactive labels include but are not limited to $Tc^{99m}$, $I^{123}$ and $In^{111}$. Such detectable labels may be attached to the ligand moiety by any conventional techniques and may be used for diagnostic purposes (e.g. imaging of tumoral cells).

In one preferred embodiment, the anti-ligand molecule is an antigen (e.g. a cell-specific antigen, a disease-specific antigen, an antigen specifically expressed on the surface of engineered target cells, . . . ) and the ligand moiety is an antibody, a fragment or a minimal recognition unit thereof (i.e. a fragment still presenting an antigenic specificity) such as those described in detail in immunology manuals (see for example Immunology, third edition 1993, Roitt, Brostoff and Male, ed Gambli, Mosby). The ligand moiety may be a monoclonal antibody. Monoclonal antibodies which will bind to many of these antigens are already known but in any case, with today's techniques in relation to monoclonal antibody technology, antibodies may be prepared to most antigens. The ligand moiety may be a part of an antibody (for example a Fab fragment) or a synthetic antibody fragment (for example, ScFv).

Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies: Techniques and Applications", J. G. R. Hurrell (CRC Press, 1982). Suitably prepared non-human antibodies may be "humanized"in known ways, for example by inserting the CDR regions of mouse antibodies into the framework of human antibodies. Additionally, as the variable heavy (VH) and variable light (VL) domains of the antibody are involved in antigen recognition, variable domains of rodent origin may be fused to constant domains of human origin such that the resultant antibody retains the antigenic specificity of the rodent parental antibody (Morrison et al (1984) Proc. Natl. Acad. Sci. USA 81, 6851-6855).

Antigenic specificity of antibodies is conferred by variable domains including Fab-like molecules (Better et al (1988) Science 240, 1041); Fv molecules (Skerra et al (1988) Science 240, 1038); ScFv molecules where the VH and VL partner domains may be linked via a flexible oligopeptide (Bird et al (1988) Science 242, 423; Huston et al (1988) Proc. Natl. Acad. Sci. USA 85, 5879) and dAbs comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

According to an advantageous embodiment, ligand moiety is selected among antibody fragments, rather than whole antibodies. Effector functions of whole antibodies, such as complement binding, are removed. ScFv and dAb antibody fragments may be expressed as fusions with other polypeptides. Minimal recognition units may be derived from the sequence of one or more of the complementary-determining regions (CDR) of the Fv fragment. Whole antibodies, and F(ab')2 fragments are "bivalent". By "bivalent" we mean that the said antibodies and F(ab')2 fragments have two antigen combining sites. In contrast, Fab, Fv, ScFv, dAb fragments and minimal recognition units are monovalent, having only one antigen combining sites.

In a further embodiment the ligand moiety is at least part of a specific moiety implicated in natural cell-surface receptor binding. Of course, said natural receptors (e.g. hormone receptors) may themselves be target cell-specific antigens and may be recognized by ligand moieties which have the property of any one of a monoclonal antibody, a ScFv, a dAb or a minimal recognition unit.

In a preferred embodiment, the ligand moiety allows to target a virally infected cell and is capable of recognizing and binding to a viral component (e.g. envelope glycoprotein) or capable of interfering with the virus biology (e.g. entry, replication . . . ). For example, the targeting of a HIV (Human Immunodeficiency Virus) infected cell can be performed with a ligand moiety specific for an epitope of the HIV envelope, such as a ligand moiety derived from the 2F5 antibody (Buchacher et al., 1992, Vaccines 92, 191-195) recognizing a highly conserved epitope of the transmembrane glycoprotein gp41 or with a ligand moiety interferring with HIV attachment to its cellular receptor CD4 (e.g. the extracellular domain of the CD4 molecule).

In another preferred embodiment, the ligand moiety allows to target a tumoral cell and is capable of recognizing and binding to a molecule related to the tumoral status, such as a tumor-specific antigen, a cellular protein differentially or over-expressed in tumoral cells or a gene product of a cancer-associated virus.

Examples of tumor-specific antigens include but are not limited to MUC-1 related to breast cancer (Hareuveni et al., 1990, Eur. J. Biochem 189, 475-486), the products encoded by the mutated BRCA1 and BRCA2 genes related to breast and ovarian cancers (Miki et al., 1994, Science 226, 66-71; Futreal et al., 1994, Science 226, 120-122; Wooster et al., 1995, Nature 378, 789-792), APC related to colon cancer (Polakis, 1995, Curr. Opin. Genet. Dev. 5, 66-71), prostate specific antigen (PSA) related to prostate cancer, (Stamey et al., 1987, New England J. Med. 317, 909), carcinoma embryonic antigen (CEA) related to colon cancers (Schrewe et al., 1990, Mol. Cell. Biol. 10, 2738-2748), tyrosinase related to melanomas (Vile et al., 1993, Cancer Res. 53, 3860-3864), receptor for melanocyte-stimulating hormone (MSH) which is expressed in high number in melanoma cells, ErbB-2 related to breast and pancreas cancers (Harris et al., 1994, Gene Therapy 1, 170-175), and alpha-foetoprotein related to liver cancers (Kanai et al., 1997, Cancer Res. 57, 461-465).

A preferred ligand moiety in use in the present invention is a fragment of an antibody capable of recognizing and binding to the MUC-1 antigen and thus targeting the MUC-1 positive tumor cells. A more preferred ligand moiety is the scFv fragment of the SM3 monoclonal antibody which recognizes the tandem repeat region of the MUC-1 antigen (Burshell et al., 1987, Cancer Res. 47, 5476-5482; Girling et al., 1989, Int J. Cancer 43, 1072-1076; Dokurno et al., 1998, J. Mol. Biol. 284, 713-728).

Examples of cellular proteins differentially or overexpressed in tumor cells include but are not limited to the receptor for interleukin 2 (IL-2) overexpressed in some lymphoid tumors, GRP (Gastrin Release Peptide) overexpressed in lung carcinoma cells, pancreas, prostate and stomach tumors (Michael et al., 1995, Gene Therapy 2, 660-668), TNF (Tumor Necrosis Factor) receptor, epidermal growth factor receptors, Fas receptor, CD40 receptor, CD30 receptor, CD27 receptor, OX-40, ∀v integrins (Brooks et al., 1994, Science 264, 569) and receptors for certain angiogenic growth factors (Hanahan, 1997, Science 277, 48). Based on these indications, it is within the scope of those skilled in the art to define an appropriate ligand moiety capable of recognizing and binding to such proteins. To illustrate, IL-2 is a suitable ligand moiety to bind to IL-2 receptor.

Suitable gene products of cancer-associated viruses include but are not limited to human papilloma virus (HPV) E6 and E7 early polypeptides as well as L1 and L2 late polypeptides (EP 0 462 187, U.S. Pat. No. 5,744,133 and WO98/04705) that are expressed in cervical cancer and EBNA-1 antigen of Epstein-Barr virus (EBV) associated with Burkitt's lymphomas (Evans et al., 1997, Gene Therapy 4, 264-267).

In still another preferred embodiment, the ligand moiety allows to target tissue-specific molecules. For example, ligand moieties suitable for targeting liver cells include but are not limited to those derived from ApoB (apolipoprotein) able to bind to the LDL receptor, alpha-2-macroglobulin able to bind to the LPR receptor, alpha-1 acid glycoprotein able to bind to the asialoglycoprotein receptor and transferrin able to bind to the transferrin receptor. A ligand moiety for targeting activated endothelial cells may be derived from the sialyl-Lewis-X antigen (able to bind to ELAM-1), from VLA-4 (able to bind to the VCAM-1 receptor) or from LFA-1 (able to bind to the ICAM-1 receptor). A ligand moiety derived from CD34 is useful to target the hematopoïetic progenitor cells through binding to the CD34 receptor. A ligand moiety derived from ICAM-1 is more intended to target lymphocytes through binding to the LFA-1 receptor. Finally, the targeting of T-helper cells may use a ligand moiety derived from HIV gp-120 or a class II MHC antigen capable of binding to the CD4 receptor.

It will be appreciated by those skilled in the art that ligand moieties which are polypeptides may be conveniently made using recombinant DNA techniques. The ligand moiety may be fused to a protein on the surface of the virus particle as disclosed below or they may be synthesized independently for example by de novo synthesis or by expression of the appropriate DNA fragment in eukaryotic as well as prokaryotic cells then coupled to the virus particle as disclosed below. The nucleic acid sequences encoding many of the ligand moieties are known, for example those for peptide hormones, growth factors, cytokines and the like and may readily be found by reference to publically accessible nucleotide sequence databases such as EMBL and GenBank. Once the nucleotide sequence is known it is obvious to the person skilled in the art how to make DNA encoding the chosen ligand moiety using, for example, chemical DNA synthetic techniques or by using the polymerase chain reaction to amplify the required DNA from genomic DNA or from tissue-specific cDNA. Many cDNAs encoding peptide hormones, growth factors, all or part of antibodies, cytokines and the like, all of which may be useful as ligand moieties, are generally commercially available.

By "target cells", we refer the cells that the modified poxviral particle of the invention can preferably infect. Depending on the nature of the ligand moiety and/or of the anti-ligand molecule, "target cells" may designate a unique type of cell or group of different types of cells having as a common feature on their surface anti-ligand molecule(s) recognized by ligand moiety(s) present onto poxviral particles of the invention. For the purpose of the invention, a target cell consists of any mammalian cell (preferably human cells) which can be infected with a poxviral particle according to the present invention. The cell may be a primary cell, a transformed cell or a tumoral cell of any origin. Suitable target cells include but are not limited to hematopoïetic cells (totipotent stem cells, leukocytes, lymphocytes, monocytes, macrophages, dendritic cells and the like), muscle cells (satellite, myocytes, myoblasts, skeletal or smooth muscle cells, heart cells), pulmonary cells, tracheal cells, hepatic cells, epithelial cells, endothelial cells or fibroblasts.

By "ligand moiety (or alternatively, anti-ligand molecule) is localized at the surface of the poxviral particle (or alternatively, of the target cells)", we shall mean that said ligand moiety (or said anti-ligand molecule) is accessible onto the surface of the poxviral particle (or of the target cells) for binding with its specific anti-ligand molecule (or respectively, ligand moiety) when said poxviral particle is contacted with said target cells. This accessibility can be measured in vitro without undue experiment using methods widely disclosed in literature.

The poxviral particle of the present invention may be obtained from any member of the poxviridae family, in particular vaccinia virus, canarypox, fowlpox, cowpox, entomopox, monkey pox, swine pox or pinguin pox. Preferably, it is a vaccinia virus particle of Copenhagen, Wyeth or Ankara modified (MVA) strain. In a general manner, numerous publications relate to the sequence and biology of the poxviruses and poxviral strains cited above. Moreover, they are available in recognized collections such as ATCC (fowlpox ATCC VR-251, monkey pox ATCC VR-267, swine pox ATCC VR-363, canarypox ATCC VR-11, cowpox ATCC VR-302) or ICTV (Canberra, Australia) (Copenhagen virus code 58.1.1.0.001; GenBank accession number M35027).

The poxviral particle of the invention may be either an IMV or an EEV form. In a preferred embodiment, it is an IMV particle. As previously indicated, an IMV particle comprises the viral core including the viral genome surrounded by a monolayer lipid envelope with viral polypeptides present at its surface including the products encoded by the A27L (p14 protein), L1R, A14L, A17L (p21 protein) D8L, A9L, E10R and H3L genes. The term "EEV" refers to an IMV particle surrounded by an additional bilayer lipid envelope exposing at its surface cellular as well as viral polypeptides including the products encoded by the B5R, A34R and HA genes.

In a advantageous embodiment, the poxviral genome may be defective in at least one gene involved in the production of EEV particles, and preferably, is defective in the F13L gene (encoding the p37 protein). It has been shown by Borrego et al. (1999, J. Gen. Virol. 80, 425-432) that the deletion of F13L gene results in a severe defect in the wrapping process of EEV, although normal levels of IMV are produced. Accordingly, by altering the poxviral F13L gene it is possible to increase IMV production. Said F13L gene may be altered by complete or partial deletion, mutation or insertion of any sequence within the coding sequence or the promoter. Optionnally, the poxviral genome may also be altered in at least one gene whose product is involved in the interaction with the natural cellular receptor mediating poxvirus uptake (e.g heparan sulfate or chondroitin sulfate). These techniques of gene alteration are well known in the art and are illustrated in Borrego et al., 1999 (supra).

The gene nomenclature used herein is that of Copenhagen vaccinia strain and is used also for the homologous genes of other poxviridae (e.g. MVA) unless otherwise indicated. However, gene nomenclature is different according to the pox strain. For information, correspondance between Copenhagen and MVA genes can be found in Table I of Antoine et al. (1998, Virol. 244, 365-396). For example, Copenhagen A27L gene is refered as 138L in MVA, both genes encoding a homologous p14-kDa protein having similar functions and localization at the IMV surface.

According to the invention, the poxviral particle are operately coupled with an heterologous ligand moiety in use in the invention. "Operately coupled" means that said particle and ligand moiety are in a relationship permitting them to function in their intended manner (i.e. the ligand moiety promotes the targeted infection specificity of the poxviral particle to the desired cell). The coupling may be made by different means that are well known to those skilled in the art including covalent, non covalent or genetic means.

Covalent coupling of ligand moieties to the surface of the poxviral particle may be performed directly through reactive functional groups or indirectly by a spacer group or other activating moiety. In particular, coupling may be done with (i) homobifunctional or (ii) heterobifunctional cross-linking reagents, with (iii) carbodiimides, (iv) by reductive amination or (vi) by activation of carboxylates (see for example Bioconjugate techniques 1996; ed G Hermanson; Academic Press).

Homobifunctional cross linkers including glutaraldehyde and bis-imidoester like DMS (dimethyl suberimidate) may be used to couple amine groups of the ligand moiety to lipid structures (e.g. of the IMV envelope) containing diacyl amines.

Many heterobifunctional cross linkers may be used in the present invention, in particular those having both amine reactive and sulfhydryl-reactive groups, carbonyl-reactive and sulfhydryl-reactive groups and sulfhydryl-reactive groups and photoreactive linkers. Suitable heterobifunctional crosslinkers are described in Bioconjugate techniques (1996) 229-285; ed G Hermanson; Academic Press) and WO99/40214. Examples of the first category include but are not limited to SPDP (N-succinimidyl3-(2-pyridyldithio)propionate), SMBP (succinimidyl-4-(p-maleimidophenyl)butyrate), SMPT (succinimidyloxycarbonyl-∀-methyl-(∀-2-pyridyldithio)toluene), MBS (m-maleimidobenzoyl-N-hydroxysuccinimide ester), SIAB (N-succinimidyl(4-iodoacetyl)aminobenzoate), GMBS ((-maleimidobutyryloxy)succinimide ester), SIAX (succinimidyl-6-iodoacetyl amino hexonate, SIAC (succinimidyl-4-iodoacetyl amino methyl), NPIA (p-nitrophenyl iodoacetate). The second category is useful to couple carbohydrate-containing molecules (e.g. env glycoproteins, antibodies) to sulfydryl-reactive groups. Examples include MPBH (4-(4-N maleimidophenyl)butyric acid hydrazide) and PDPH (4-(N-maleimidomethyl) cyclohexane-1-carboxyl-hydrazide ($M_2C_2H$ and 3-2(2-pyridyldithio)proprionyl hydrazide). As an example of the third category, one may cite ASIB (1-(p azidosalicylamido)-4-(iodoacetamido)butyrate). Another alternative includes the thiol reactive reagents described in Frisch et al. (Bioconjugate Chem. 7 (1996) 180-186).

Coupling (iii) involves, e.g., amine groups of diacyl amines present in lipid structures that can participate in the carbodiimide reaction with carboxylate groups of the ligand moiety.

Coupling (iv) may-be performed, e.g., via imine formation followed by reduction using a cyanoborohydrate.

Coupling (vi) may involve, e.g., an NHS ester derivative of ligand moiety and poxvirus amine groups to produce stable amide bond linkages.

Another example uses a maleimide-sulfhydryl bond involving a sulfhydryl group and a sulfhydryl reactive group. For example SATA (N-succinimidyl S-acelythioacetate) can be used to introduce a sulfhydryl group whereas sulfo SMCC (sulfosuccinimidyl 4-(N-maleimidomethyl)cyclo hexane 1-carboxylate) can be used to introduce a maleimide group resulting in a covalent thioether bond.

Covalent coupling may also be performed using a polymer such as polyethylene glycol (PEG) or its derivatives. Preferably, the polymer has an average molecular weight comprised between 200 to 20000 Da. For example, tresyl-MPEG can be used to couple an amino group present on Lys residues (see for example WO99/40214). Other means to conjugate two partners via PEG are described in the literature (in Bioconjugate techniques (1996) 606-618; ed G Hermanson; Academic Press and Frisch et al. Bioconjugate Chem. 7 (1996) 180-186).

Non covalent coupling includes electrostatic interactions, for example between a cationic ligand moiety and a negatively charged poxvirus. Another alternative consists in using affinity components such as Protein A, biotin/avidin, antibodies, which are able to associate non covalently or by affinity both partners. For example, coupling between a peptide ligand moiety and a poxviral particle may use biotinylated antibodies directed against a surface-exposed epitope and streptavidin-labelled antibodies directed against the peptide ligand moiety according to the technique disclosed by Roux et al. (1989, Proc. Natl. Acad Sci USA 86, 9079). Bifunctional antibodies directed against each of the coupling partners are also suitable for this purpose.

Genetic coupling is intended for coupling a ligand moiety which is a polypeptide or a fragment thereof. Advantageously, a nucleic acid encoding said ligand moiety is fused to a viral nucleic acid sequence encoding a homologous poxviral polypeptide localized at the surface of the non modified poxviral particle. However, the invention further concerns a genetic coupling wherein a nucleic acid encoding a ligand moiety is fused to a nucleic acid sequence encoding an heterologous polypeptide (e.g. an membrane anchoring polypeptide) permitting to localize said ligand moiety at the surface of the poxviral particle. Preferably, the nucleic acid encoding the ligand moiety is fused in regions of the viral genome that are non essential for poxvirus integrity.

According to a first alternative, the genetic coupling results in a chimeric polypeptide wherein at least a portion of the surface-exposed homologous poxviral polypeptide is removed and replaced by the heterologous ligand moiety in use in the present invention. According to a second alternative, the genetic coupling results in a chimeric polypeptide wherein the heterologous ligand polypeptide moiety in use in the present invention is incorporated in the surface-exposed homologous poxviral polypeptide. Polypeptide fusion resulting from genetic coupling can be made at any location, at the N-terminus, the C-terminus or between two amino acid residues of the viral polypeptide. Preferably the selected genetic coupling site (i.e. the site of the viral nucleic acid where the ligand moiety encoding sequence is inserted) does not disrupt the corresponding open reading frame.

When the poxviral particle of the invention is an IMV, homologous surface-exposed poxviral polypeptides suitable for these genetic coupling include but are not limited to the expression products of the A27L (p14 protein), L1R, A14L, A17L (p21 protein), D8L, A9L, E10R and H3L genes. According to a preferred embodiment, the nucleotide sequence encoding the ligand moiety is fused with the A27L gene sequence so that said ligand moiety is finally located at the N-terminus of the p14. Preferably, said ligand moiety encoding nucleotide sequence is fused immediately downstream of the A27L gene initiator codon.

When the poxviral particle of the invention is an EEV, homologous surface-exposed poxviral polypeptides suitable for these genetic coupling include but are not limited to the expression products of the B5R, A34R and HA genes. According to a preferred embodiment, the nucleotide sequence encoding the ligand moiety is fused with the B5R gene sequence so that said ligand moiety is finally located at the N-terminus of the corresponding expression product. Preferably, said ligand moiety encoding nucleotide sequence is fused immediately downstream of the B5R gene initiator codon.

According to the present invention, the ligand moiety and the poxviral particle may be further modified to improve or stabilize the coupling. In particular, the ligand moiety may present a spacer moiety at one of its extremities to facilitate its accessibility towards the target cells. Moreover, the poxviral particle according to the invention may comprise one or more ligand moiety that may or may not be combined one to another, for example in a tandem structure. For example, when it is desirable to enhance the specificity of the poxviral particle towards specific target cells, it may be advantageous to use a combination of ligand moieties capable of recognizing and binding to such target cells.

In accordance with the objectives pursued by the present invention, the ligand moiety may comprise a signal peptide facilitating its insertion in the envelope of the poxviral particle. Although the use of an hydrophobic sequence allowing for membrane anchorage can be envisaged, it is preferable to use a signal peptide allowing translocation to the trans-Golgi network. Such a peptide can be isolated or identified from any protein naturally present in the Golgi compartment (see for example Mochamer et Rose, 1987, J. Cell Biol. 105, 1205-1214; Mochamer, 1993, Curr. Opin. Cell Biol. 5, 606-612; Muesch et al., 1990, Trends Biochem sci 15, 86-88). The signal peptide can include one or several modification(s) with respect to the native sequence provided that its function is not significantly altered. A preferred signal peptide in use in the present invention is derived from the human trans-Golgi network glycoprotein TGN51 (Kain et al., 1997, J. Biol. Chem. 273, 981-988). It is preferably incorporated by genetic coupling at the N-terminus of the ligand moiety. Preferably the ligand moiety is genetically to a viral polypeptide.

Although it is possible to obtain empty poxviral particle (also called pseudo-poxviral particle) displaying the specific infection property above-described, according to a preferred embodiment, the poxviral particle of the invention comprises at least a nucleic acid of interest, particularly a recombinant nucleic acid including at least one therapeutic gene placed under the control of the elements allowing its expression in eukaryotic target cells. However, empty poxviral particles, or pseudo-poxviral particle, of the invention may be used in forming complexes with nucleic acid of interest for facilitating its targeted cellular uptake such as disclosed in U.S. Pat. No. 5,928,944 and WO 9521259.

The term "nucleic acid" within the present invention is intended to designate any possible nucleic acid, in particular both DNA, RNA or an hybrid form, single or double stranded, linear or circular, natural or synthetic, modified or not (see U.S. Pat. Nos. 5,525,711, 4,711,955 or EP-A 302 175 for modification examples). It may be, inter alia, a genomic DNA, a genomic RNA, a cDNA, an mRNA, an antisense RNA, a ribosomal RNA, a ribozyme, a transfer RNA or DNA encoding such RNAs. The nucleic acid may be in the form of a plasmid or linear nucleic acid which contains at least one expressible sequence that can generate a polypeptide, a ribozyme, an antisense RNA or another molecule of interest upon delivery to a cell. The nucleic acid can also be an oligonucleotide (i.e. a nucleic acid having a short size of less than 100 bp) which is to be delivered to the cell, e.g., for antisense or ribozyme functions. Preferably, the nucleic acid is in the form of a poxviral genomic DNA.

If the nucleic acid contains the proper genetic informations when it is placed in an environment suitable for gene expression, its transcriptional unit will thus express the encoded gene product. The level and cell specificity of expression will depend to a significant extent on the strength and origin of the associated promoter and the presence and activation of an associated enhancer element. Thus in a preferred embodiment, the transcriptional control element includes the promoter/enhancer sequences such as CMV promoter/enhancer. However, those skilled in the art will recognise that a variety of other promoter and/or enhancer sequences are known which may be obtained from any viral, prokaryotic, e.g. bacterial, or eukaryotic, which constitutive or regulable, which are suitable for expression in eukaryotic cells, and particularly in target cells. More precisely, these genetic informations necessary for expression by a target cell comprise all the elements required for transcription of said DNA into mRNA and, if necessary, for translation of mRNA into polypeptide. Transcriptional promoters suitable for use in various vertebrate systems are widely described in literature. For example, suitable promoters include viral promoters like RSV, MPSV, SV40, CMV or 7.5 k, vaccinia promoter, inducible promoters, etc. Preferred promoters are isolated from poxviruses e.g. 7.5K, H5R, TK, p28, p11 or K1L of vaccinia virus. Alternatively, one may use a synthetic promoter such as those described in Chakrabarti et al. (1997, Biotechniques 23, 1094-1097), Hammond et al. (1997, J. Virological Methods 66, 135-138) and Kumar and Boyle (1990, Virology 179, 151-158) as well as chimeric promoters between early and late poxviral promoters.

The nucleic acid may further includes additional functional elements, such as intron sequences, targeting sequences, transport sequences, secretion signal, nuclear localization signal, IRES, poly A transcription termination sequences, tripartite leader sequences, sequences involved in replication or integration. Said sequences have been reported in the literature and can be readily obtained by those skilled in the art.

In a preferred embodiment, the nucleic acid of interest contains at least one sequence of interest encoding a gene product which is a therapeutic molecule (i.e. a therapeutic gene). A "therapeutic molecule" is one which has a pharmacological or protective activity when administered appropriately to a patient, especially patient suffering from a disease or illness condition or who should be protected against this disease or condition. Such a pharmacological or protective activity is one which is expected to be related to a beneficial effect on the course or a symptom of said disease or said condition. When the skilled man selects in the course of the present invention a gene encoding a therapeutic molecule, he generally relates his choice to results previously obtained and can reasonably expect, without undue experiment other than practicing the invention as claimed, to obtain such pharmacological property. According to the invention, the sequence of interest can be homologous or heterologous to the target cells into which it is introduced. Advantageously said sequence of interest encodes all or part of a polypeptide, especially a therapeutic or prophylactic polypeptide giving a therapeutic or prophylactic property. A polypeptide is understood to be any translational product of a polynucleotide regardless of size, and whether glycosylated or not, and includes peptides and proteins. Therapeutic polypeptides include as a primary example those polypeptides that can compensate for defective or deficient proteins in an animal or human organism, or those that act through toxic effects to limit or remove harmful cells from the body. They can also be immunity conferring polypeptides which act as endogenous antigen to provoke a humoral or cellular response, or both.

Examples of polypeptides encoded by a therapeutic gene include genes coding for a cytokine (alpha, beta or gamma interferon, interleukin, in particular IL-2, IL-6, IL-10 or IL-12, a tumor necrosis factor (TNF), a colony stimulating factor GM-CSF, C-CSF, M-CSF . . . ), a immunostimulatory polypeptide (B7.1, B7.2 and the like), a coagulation factor (FVIII, FIX . . . ), a growth factor (Transforming Growth Factor TGF, Fibroblast Growth Factor FGF and the like), an enzyme (urease, renin, thrombin, metalloproteinase, nitric oxide synthase NOS, SOD, catalase . . . ), an enzyme inhibitor (alphal-antitrypsin, antithrombin III, viral protease inhibitor, plasminogen activator inhibitor PAI-1), the CFTR (Cystic Fibrosis Transmembrane Conductance Regulator) protein, insulin, dystrophin, a MHC antigen of class I or II, a polypeptide that can modulate/regulate expression of cellular genes, a polypeptide capable of inhibiting a bacterial, parasitic or viral infection or its development (antigenic polypeptides, antigenic epitopes, transdominant variants inhibiting the action of a native protein by competition . . . ), an apoptosis inducer or inhibitor (Bax, Bc12, Bc1X . . . ), a cytostatic agent (p21, p 16, Rb . . . ), an apolipoprotein (ApoAI, ApoAIV, ApoE . . . ), an inhibitor of angiogenesis (angiostatin, endostatin . . . ), an angiogenic polypeptide (family of Vascular Endothelial Growth Factors VEGF, FGF family, CCN family including CTGF, Cyr61 and Nov), an oxygen radical scaveyer, a polypeptide having an anti-tumor effect, an antibody, a toxin, an immunotoxin and a marker (beta-galactosidase, luciferase . . . ) or any other genes of interest that are recognized in the art as being useful for the treatment or prevention of a clinical condition.

In view of treating an hereditary dysfunction, one may use a functional allele of a defective gene, for example a gene encoding factor VIII ou IX in the context of haemophilia A or B, dystrophin (or minidystrophin) in the context of myopathies, insulin in the context of diabetes, CFTR in the context of cystic fibrosis.

Suitable anti-tumor genes include but are not limited to those encoding tumor suppressor genes (e.g. Rb, p53, DCC, NF-1, Wilm's tumor, NM23, BRUSH-1, p16, p21, p56, p73 as well as their repective mutants), suicide gene products, antibodies, polypeptides inhibiting cellular division or transduction signals.

In a preferred embodiment, the therapeutic gene is a suicide gene encoding an expression product able to transform an inactive substance (prodrug) into a cytotoxic substance, thereby giving rise to cell death. The gene encoding the TK HSV-1 constitutes the prototype of the suicide gene family (Caruso et al., 1993, Proc. Natl. Acad. Sci. USA 90, 7024-7028; Culver et al., 1992, Science 256, 1550-1552). While the TK polypeptide is non toxic as such, it catalyzes the transformation of nucleoside analogs (prodrug) such as acyclovir or ganciclovir. The transformed nucleosides are incorporated into the DNA chains which are in the process of elongation, cause interruption of said elongation and therefore inhibition of cell division. A large number of suicide gene/prodrug combinations are currently available. Those which may more specifically be mentioned are rat cytochrome p450 and cyclophosphophamide (Wei et al., 1994, Human Gene Ther. 5, 969-978), *Escherichia coli* (*E coli*) purine nucleoside phosphorylase and 6-methylpurine deoxyribonucleoside (Sorscher et al., 1994, Gene Therapy 1, 223-238), *E. coli* guanine phosphoribosyl transferase and 6-thioxanthine (Mzoz et al., 1993, Human Gene Ther. 4, 589-595). However, in a more preferred embodiment, the poxviral particle of the invention comprises a suicide gene encoding a polypeptide having a cytosine deaminase (CDase) or a uracil phosphoribosyl transferase (UPRTase) activity or both CDase and UPRTase activities, which can be used with the prodrug 5-fluorocytosine (5-FC). The use of a combination of suicide genes, e.g. encoding polypeptides having CDase and UPRTase activities, can also be envisaged in the context of the invention.

CDase and UPRTase activities have been demonstrated in prokaryotes and lower eukaryotes, but are not present in mammals. CDase is normally involved in the pyrimidine metabolic pathway by which exogenous cytosine is transformed into uracil by means of a hydrolytic deamination, whereas UPRTase transforms uracile in UMP. However, CDase also deaminates an analog of cytosine, 5-FC, thereby forming 5-fluorouracil (5-FU), which is highly cytotoxic when it is converted into 5-fluoro-UMP (5-FUMP) by UPRTase action.

Suitable CDase encoding genes include but are not limited to the *Saccharomyces cerevisiae*FCY1 gene (Erbs et al., 1997, Curr. Genet. 31, 1-6; WO93/01281) and the *E. coli* codA gene (EP 402 108). Suitable UPRTase encoding genes include but are not limited to those from *E. coli* (upp gene; Anderson et al., 1992, Eur. J. Biochem. 204, 51-56), *Lactococcus lactis* (Martinussen and Hammer, 1994, J. Bacteriol. 176, 6457-6463), *Mycobacterium bovis* (Kim et al. 1997, Biochem Mol. Biol. Int 41, 1117-1124), *Bacillus subtilis* (Martinussen et al. 1995, J. Bacteriol. 177, 271-274) and *Saccharomyces cerevisiae* (FUR-1 gene; Kern et al., 1990, Gene 88, 149-157). Preferably, the CDase encoding gene is derived from the FCY-1 gene and the UPRTase encoding gene is derived from the FUR-1 gene.

The present invention also encompasses the use of mutant suicide genes, modified by addition, deletion and/or substitution of one or several nucleotides providing that the cytotoxic activity of the gene product be preserved. A certain number of CDase and UPRTase mutants have been reported in the literature including a fusion protein which encodes a two domain enzyme possessing both CDase and UPRTase activities (WO96/16183) as well as a mutant of the UPRTase encoded by the FUR-1 gene having the first 35 residues deleted (mutant FCU-1 disclosed in WO99/54481).

As mentioned above, therapeutic genes is also to be understood to include antisense sequences and ribozyme encoding genes capable of binding and destroying the RNA of selected positively-acting growth regulatory genes, such as oncogenes and protooncogenes (c-myc, c-fos, c-jun, c-myb, c-ras, Kc and JE).

The nucleic acid incorporated into the poxviral particle of the present invention may comprise one or more therapeutic gene(s). In this regard, the combination of genes encoding a suicide gene product and a cytokine gene (e.g. α, ∃ or γ interferons, interleukins, preferably selected among IL-2, IL-4, IL-6, IL-10 or IL-12, TNF factors, GM-CSF, C-CSF, M-CSF . . . ), an immunostimulatory gene (e.g. B7.1, B7.2, ICAM) or a chimiokine gene (e.g. MIP, RANTES, MCP 1, . . . ) is advantageous. The different gene expression may be controlled by a unique promoter (polycistronic cassette) or by independent promoters. Moreover, they may be inserted in a unique site or in various sites along the nucleic acid either in the same or opposite directions.

In another embodiment, the present invention further concerns a vector comprising at least one nucleotide sequence encoding a chimeric protein comprising (i) at least an heterologous ligand moiety as previously described, and (ii) all or part of an homologous viral polypeptide naturally localized at the surface of a poxviral particle as previously disclosed. Of course, the nucleotide sequence is placed under the control of elements which are necessary for its expression. The choice of the vector according to the invention is wide and accessible to the persons skilled in the art. The vector may be a plasmid, or a viral vector derived from any animal virus, especially an adenovirus, a retrovirus, an AAV (adenovirus associated virus) or a poxvirus. According to a preferred embodiment, the vector of the invention is a poxviral vector (i.e. a poxviral genome DNA, especially a VV or MVA genome DNA). The term "part" as used herein refers to a fragment of the viral polypeptide which allows exposition of the ligand moiety at the surface of a viral vector. Moreover, a vector according to the present invention may also include at least one nucleotide sequence of interest.

The basic technique for inserting into a viral genome the sequences of interest and associated elements required for expression is described in numerous documents accessible to the man skilled in the art (Piccini et al., 1987, Methods of Enzymology 153, 545-563; U.S. Pat. Nos. 4,769,330; 4,772, 848; 4,603,112; 5,100,587 and 5,179,993). This technique relates to homologous recombination events between overlapping sequences in a viral genome (i.e. desired insertion site) and a plasmid encompassing the sequence of interest.

The insertion site within the poxviral genome is preferably a nonessential locus, in order that the recombinant poxvirus remains viable and infectious. Suitable nonessential regions include but are not limited to non-coding intergenic regions or any gene for which inactivation or deletion does not significantly impair viral growth, replication or infection. One may also envisage insertion in an essential viral locus provided that the defective function be supplied in trans during production of viral particles, for example by using an helper cell line carrying the complementing sequences corresponding to those deleted in the poxviral genome.

For example, when using the Copenhagen vaccinia virus, one will preferably select an insertion site localized within the thymidine kinase gene (tk) (Hruby et al., 1983, Proc. Natl. Acad. Sci USA 80, 3411-3415; Weir et al., 1983, J. Virol. 46, 530-537). However, other insertion sites are also appropriate, such as within the hemagglutinin gene (Guo et al., 1989, J. Virol. 63, 4189-4198), within the K1L locus, within the u gene (Zhou et al., 1990, J. Gen. Virol. 71, 2185-2190) or at the left end of the vaccinia virus genome where a variety of spontaneous or engineered deletions have been reported in the literature (Altenburger et al., 1989. Archives Virol. 105, 15-27; Moss et al. 1981, J. Virol. 40, 387-395; Panicali et al., 1981, J. Virol. 37, 1000-1010; Perkus et al, 1989, J. Virol. 63, 3829-3836; Perkus et al, 1990, Virol. 179, 276-286; Perkus et al, 1991, Virol. 180, 406-410).

When using MVA, one will preferably select an insertion site localized within anyone of the identified deletions I to VII, and preferably in deletion II or III (Meyer et al., 1991, J. Gen. Virol. 72, 1031-1038; Sutter et al., 1994, Vaccine 12, 1032-1040) as well as within the D4R locus.

When using fowlpox virus, although insertion within the thymidine kinase gene may be considered, the sequence of interest is preferably introduced into a non-coding intergenic region e.g., the intergenic region situated between ORFs 7 and 9 of the 1.3 kb HindIII fragment of the fowlpox genome (see for example EP 314 569 and U.S. Pat. No. 5,180,675).

The present invention further provides a process of producing a poxviral particle according to the invention, comprising the steps of:
a) obtaining a seed of said poxviral particle,
b) preparing a culture of permissive cells,
c) infecting said cell culture with said seed of poxviral particle,
d) culturing said infected cells for an appropriate period of time, e) recovering the poxviral particles produced from the cell culture and/or the culture supernatant, and
f) optionally, purifying the recovered poxviral particles.

According to a special embodiment, it is possible to combine step a) and c). In this case, the process of the invention comprises the steps of:
a) preparing a culture of permissive cells,
b) infecting said cell culture with a wild type poxviral particle and transfecting said cell with a plasmid comprising a sequence of interest flanked by overlapping sequences capable of homologous recombination with the DNA genome of said poxvirus,
c) culturing said cells for an appropriate period of time, d) recovering the poxviral particles produced from the cell culture and/or the culture supernatant, and e) optionally, purifying the recovered poxviral particles.

In a preferred embodiment, the "permissive cells" are primary chicken embryo fibroblasts (CEF) prepared from chicken embryos obtained from fertilized eggs. According to the particular embodiment where the poxviral genome of the particle is defective for one or more viral functions (e.g. defective in at least one gene involved in the production of EEV particles) it may be advantageous to use helper cells providing in trans the defective function. In particular, poxviruses defective for function encoded by the F13L gene are preferably cultured on a cell line expressing the F13L expression product. Such a cell line can be generated by transfection of a appropriate vector expressing the F13L polypeptide as described in Borrego et al. (1999, J. Gen. Virol. 80, 425-432). According to an advantageous embodiment, isolation and propagation of a poxviral particle of the present invention can be performed on a target cell line exhibiting at its surface the anti-ligand molecule recognized by the ligand moiety of the present invention. This allows to minimize possible contamination with the wild type genome. For example, a poxvirus particle having a ligand moiety specific for MUC-1 polypeptide is preferably propagated on MUC-1 expressing target cells. The construction of such cell lines expressing onto their surface an anti-ligand molecule is within the scope of a man skilled in the art.

The "seed of poxviral particle" is obtained according to the usual techniques at the end of the homologous recombination events between the poxviral genome and the plasmid incorporating the sequence of interest. With this respect, one can for example refer to the Experimental section of the present specification.

In case where additional transfection of the cells with a plasmid is required, various widely used cell transfecting methods can be used (e.g. DNA precipitation with calcium, electrotransfection, . . . ) optionally combined with a glycerol which may facilitate the plasmid uptake. Additionally, a selection step can be included where the recombinant virus contains a selection gene (e.g. *E. coli* gpt gene), for example, by using a selective culture medium containing a mixture of mycophenolic acid, xanthin and hypoxanthin in step c).

While the viral particles can be recovered from the culture supernatant, they can also be recovered from the cells. One of the commonly used methods consists in lysing the cells by any means (chemical, freezing/thawing, osmotic shock, mecanic shock, sonication and the like). The poxviral particle of the invention can be isolated by consecutive rounds of plaque purification and then purified using the techniques of the art (chromatographic methods, ultracentrifugation on cesium chloride or sucrose gradient). Alternatively, the affinity between the ligand moiety displayed at the viral surface and its anti-ligand may be used for purifiying the poxviral particle of the present invention. For example, the purification may be performed by a) immobilizing the concerned anti-ligand onto a solid support, b) contacting the viral preparation with the immobilized anti-ligand for a sufficient period of time to allow specific binding between the anti-ligand and the ligand moiety, c) discarding the unbound material and d) eluting the bound material and e) recovering the eluted material. Such a purification can be advantageous to reduce an eventual contamination of the poxviral particles of the invention with wild type or helper poxviruses.

The process of the invention can be used to produce both IMV and EEV poxviral particles. According to a preferred embodiment of the invention, the process includes an supplemental step allowing breakage of the additional envelope of EEV and selective production of IMV. Preferably, said further step consists in a sonication step or solubilization step in a mild detergent (e.g. Brij-58).

The invention also relates to a composition comprising at least one poxviral particle and/or at least one vector according to the invention. In a special case, the composition comprises two or more poxviral particles, and/or two or more vectors of the invention, wherein they differ each from one another by (i) the nature of the heterologous ligand moiety and/or (ii) the nature of the nucleic acid or of sequence of interest and/or (iii) the poxviral origin and/or (iv) the particle form (IMV/EEV). This composition can be in various forms, e.g. in solid, liquid, powder, aqueous, lyophilized form. In a preferred embodiment, this composition further comprises a pharmaceutically acceptable carrier, allowing its use in a method for the therapeutic treatment of humans or animals. In this particular case, the carrier is preferably a pharmaceutically suitable injectable carrier or diluent (for examples, see Remington's Pharmaceutical Sciences, $16^{th}$ ed. 1980, Mack Publishing Co). Such carrier or diluent is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g. Tris-HC1, acetate, phosphate), emulsifiers, solubilizers or adjuvants. The pH of the pharmaceutical preparation is suitably adjusted and buffered in order to be useful in in vivo applications. It may be prepared either as a liquid solution or as a solid form (e.g. lyophilized) which can be suspended in a solution prior to administration. Representative examples of carriers or diluents for an injectable composition include water, isotonic saline solutions which are preferably buffered at a physiological pH (such as phosphate buffered saline or Tris buffered saline), mannitol, dextrose, glycerol and ethanol, as well as polypeptides or proteins such as human serum albumin. For example, such a composition may comprise 10 mg/ml mannitol, 1 mg/ml HSA, 20 mM Tris pH 7.2 and 150 mM NaCl.

A composition according to the invention may be manufactured in a conventional manner for local, systemic, oral, rectal or topical administration. Suitable routes of administration include but are not limited to intragastric, subcutaneous, aerosol, instillation, inhalation, intracardiac, intramuscular, intravenous, intraarterial, intraperitoneal, intratumoral, intranasal, intrapulmonary or intratracheal routes. The administration may take place in a single dose or a dose repeated one or several times after a certain time interval. The appropriate administration route and dosage vary in accordance with various parameters, for example, with the condition or disease involved, the need for prevention or therapy, the stage to which it has progressed and the therapeutic gene to be transferred. As an indication, the poxviral particles may be formulated in the form of doses of between $10^4$ and $10^{14}$ pfu (plaque forming units), advantageously between $10^5$ and $10^3$ pfu and preferably between $10^6$ and $10^{12}$ pfu. The titer may be determined by conventional techniques. The vector doses are preferably comprised between 0.01 and 10 mg/kg, more especially between 0.1 and 2 mg/kg.

In addition, a composition according to the present invention may include one or more stabilizing substance(s), such as lipids (e.g. cationic lipids, liposomes, lipids as described in WO98/44143), nuclease inhibitors, polymers, chelating agents in order to preserve its degradation within the animal/human body.

In another embodiment, the present invention provides the use of a poxviral particle or of a vector according to the invention, for the preparation of a drug intended for the treatment of human or animal organism by gene therapy. Within the scope of the present invention, "gene therapy" has to be understood as a method for introducing any therapeutic gene into a cell. Thus, it also includes immunotherapy that relates to the introduction of a potentially antigenic epitope into a cell to induce an immune response which can be cellular or humoral or both.

The use according to the invention is dependent upon the targeting properties of the ligand moiety displayed at the surface of the poxviral particle or expressed by the vector of the invention. Thus, a ligand moiety capable of recognizing and binding to a molecule present at the surface of a cell infected with a pathogenic agent (bacteria, virus or parasite) is appropriate for the treatment or prevention of any condition or disease caused by such an infection. A tumor targeting ligand moiety is more intended in the treatment or the prevention of a cancer. The term "cancer" encompasses any cancerous conditions including diffuse or localized tumors, metastasis, cancerous polyps and preneoplastic lesions (e.g. dysplasies) as well as diseases which result from unwanted cell proliferation. One may cite more particularly cancers of breast, cervix (in particular those induced by a papilloma virus), prostate, lung, bladder, liver, colorectal, pancreas, stomach, esophagus, larynx, central nervous system, blood (lymphomas, leukemia, etc.), melanomas and mastocytoma.

The invention further provides a method for the treatment of a human or animal organism, comprising administering to said organism a therapeutically effective amount of a poxviral particle, of a vector or of a composition according to the invention. A <<therapeutically effective amount>> is a dose sufficient to the alleviation of one or more symptoms normally associated with the disease or condition desired to be treated. When prophylactic use is concerned, this term means a dose sufficient to prevent or delay the establishment of a disease or condition.

The method of the present invention can be used for preventive purposes and for therapeutic applications relative to the diseases or conditions listed above. The present method is particularly useful to prevent establishment of tumors or to reverse existing tumors of any type, using an approach similar to that described herein. It is to be understood that the present method can be carried out by any of a variety of approaches. Advantageously, the poxviral particle, the vector or the composition of the invention can be administered directly in vivo by any conventional and physiologically acceptable administration route, for example by intravenous injection, into an accessible tumor, into the lungs by means of an aerosol or instillation, into the vascular system using an appropriate catheter, etc. The ex vivo approach may also be adopted which consists in removing cells from a patient (bone marrow cells, peripheral blood lymphocytes, myoblasts and the like . . . ), introducing the poxviral particle or the vector of the invention in accordance with the techniques of the art and readministering them to the patient.

In the case of in vivo treatment according to the invention, in order to improve the transfection rate, the patient may undergo a macrophage depletion treatment prior to administration of the pharmaceutical preparations described above. Such a technique is described in the literature (refer particularly to Van Rooijen et al., 1997, TibTech, 15, 178-184).

According to the preferred embodiment, when the method of the invention uses a recombinant poxviral particle presenting the characteristics of the invention and expressing a suicide gene, it can be advantageous to additionally administer a pharmaceutically acceptable quantity of a prodrug which is specific for the expressed suicide gene product. The two administrations can be made simultaneously or consecutively, but preferably the prodrug is administered after the poxviral particle of the invention. By way of illustration, it is possible to use a dose of prodrug from 50 to 500 mg/kg/day, a dose of 200 mg/kg/day being preferred. The prodrug is administered in accordance with standard practice. The oral route is preferred. It is possible to administer a single dose of prodrug or doses which are repeated for a time sufficiently long to enable the toxic metabolic to be produced within the host organism or the target cell. As mentioned above, the prodrug ganciclovir or acyclovir can be used in combination with TK HSV-1 gene product and 5-FC in combination with FCY1, FUR1 and/or FCU1 gene product.

To illustrate a method intended for tumor treatment, one may first administer a poxviral particle expressing a suicide gene and displaying at its surface a ligand moiety capable of recognizing and binding to a tumor antigen expressed by the tumoral cells. Once infected, the cancerous cells will express the suicide gene. Killing of the infected cells can be performed by administering the prodrug metabolized by the chosen suicide gene product. In individuals in whom prevention or reversal of MUC-1 positive breast cancer is desired, one may employ a poxviral particle expressing FCU-1 and harboring at its surface a SM3 scFv ligand capable of recognizing and binding to the MUC-1 tumor antigen. Killing of the MUC-1 positive infected cells may be achieved with further administration of the prodrug 5-FC.

In addition, one particular characteristic of the method of the invention is that the poxviral particle of the invention can be produced in vivo in the treated organism. With this respect, one may envisage to administer to the patient an IMV poxviral particle which does not exhibit at its surface the ligand moiety but contain a poxviral genome genetically engineered by insertion of a nucleic acid encoding such a ligand moiety in a sequence encoding a polypeptide localized at the surface of the EEV poxviral particle (e.g. the B5R gene). Accordingly, in this special embodiment, the recombinant poxviral genome is able to produce in vivo (i.e. after administration to the patient) EEV particles in accordance with the present invention while the administered IMV form still presents the wild type poxviral characteristics. Said administered IMV particles infecting the patient cells in a non-specific manner (non targeted cells), the viral genome will replicate in the host infected cells and release EEV particles capable of infecting only target cells.

Prevention or treatment of a disease or a condition can be carried out using the present method alone or, if desired, in conjunction with presently available methods (e.g. radiation, chemotherapy and surgery).

The infection specificity of the poxviral particles of the invention is actually related to the binding specificity of the ligand moiety localized onto their surface. Accordingly, said poxviral particles can be used in methods based on specific binding between a said ligand moiety and an anti-ligand molecule. Thus, the invention also relates to a method for detecting and/or separating and/or concentrating and/or purifying and/or assaying any anti-ligand molecule, or by extension any compound comprising such an anti-ligand molecule, present in a sample, in which a poxviral particles according to the invention (i.e. exhibiting at their surface an heterologous ligand moiety which is able to specifically bind to such a molecule) is used to form a binding complex with said anti-ligand molecule, or said compound, if they are present in the sample.

The invention also concerns a reagent for detecting and/or concentrating and/or separating and/or purifying and/or assaying in a sample any anti-ligand molecule, or by extension any compound including such an anti-ligand molecule, comprising a poxviral particles according to the present invention i.e. exhibiting at their surface an heterologous ligand moiety which is able to specifically bind to such a molecule or compound.

The invention relates in particular to a method for detecting and/or concentrating and/or separating and/or purifying and/or assaying any anti-ligand molecule, or by extension any compound comprising such an anti-ligand molecule in a sample, including the following steps: said sample is placed in contact with a reagent according to the invention under conditions permitting a binding reaction, then any binding complex formed is separated, possibly detected, and/or quantified.

More particularly, the present invention relates to a method for detecting and/or concentrating and/or separating and/or purifying and/or assaying any anti-ligand molecule, or by extension any compound comprising such an anti-ligand molecule, present in a sample, using a reagent according to the invention comprising the steps of:

a) immobilizing said reagent onto a solid support,
b) contacting said sample with said immobilized reagent for a sufficient time to allow specific binding of the anti-ligand molecule, or compound comprising the anti-ligand molecule, with the heterologous ligand moiety of said reagent,
c) discarding the unbound sample,
d) eluting the anti-ligand molecule, or compound comprising the anti-ligand molecule, retained in step b), and
e) analyzing said anti-ligand molecule, or compound comprising the anti-ligand molecule, eluted in step d).

The term "solid support" as used here is, without limitation, in the form of a microtitration slide, a foil, a column, a sheet, a cone, a well, a bead, or any other appropriate micro or macro-particulate substrate, and includes all materials on which viral particle of the invention can be immobilized. This may be synthetic materials which are chemically modified or otherwise, especially polysaccharides, such as cellulose materials, for example paper, cellulose derivatives such as nitrocellulose and cellulose acetate or dextran (BIAcore, Upsala, Sweden); polymers such as vinyl chloride, polyethylene, polystyrene, polyacrylate, or copolymers such as propylene and vinyl chloride polymer, vinyl chloride and vinyl acetate polymer; styrene-based copolymers; natural fibers such as cotton and synthetic fibers such as nylon.

Preferably, the "solid support" is a polystyrene polymer, a butadiene/styrene copolymer or a butadiene/styrene copolymer mixed with one or more polymers or copolymers chosen from polystyrene, styrene/acrylonitrile or styrene/methyl methacrylate copolymers, polypropylenes, polycarbonates and the like.

The reagent (i.e. comprising the viral particles of the invention) can be attached to the solid support directly or indirectly.

Using the direct manner, two approaches are possible: either by adsorption of the reagent onto the solid support, that is to say by noncovalent bonds (principally of the hydrogen, Van der Walls or ionic type), or by formation of covalent bonds between the reagent and the support. Indirectly, it is possible to pre-attach an "anti-reagent" compound (by adsorption or covalence) to the substrate, said compound being able to interact with the reagent such as to immobilize the system on the solid substrate. By way of example, there may be mentioned an antibody, on the condition that it is immunologically reactive with a portion of the poxviral particles different from that involved in the binding with anti-ligand molecules; a ligand-receptor system, for example by grafting onto the poxviral particles a molecule such as a vitamin, and by immobilizing onto the solid phase the corresponding receptor (for example the biotin-streptavidin system). Indirect manner is also understood to mean the preliminary grafting or fusion by genetic coupling of a protein, or a fragment of this protein, or of a polypeptide, to one end of the poxviral particle proteins, and the immobilization of the latter onto the solid support by passive adsorption or covalent bonding of the protein or of the polypeptide grafted or fused.

In the context of the process of the present invention, the term "anti-ligand molecule, or by extension any compound comprising such an anti-ligand molecule" is used broadly to designate an organic chemical such as a drug or a polypeptide which may be contained in a sample or any target cells as previously defined, and more particularly tumoral cells. For example, it can designate a non-naturally occurring molecule which can be produced as a result of in vitro or synthetic method. It can be a naturally occurring molecule present in a cellular or biological sample (cultured cells, cell, organs or tissue biopsie, body fluids and the like), such as antibodies, cellular receptors, viral receptors and tumoral markers. If desired the sample can be processed using a method such as HPLC, which can provide a fraction enriched in molecules having a defined range of molecular weight, hydrophilic characteristics or the like. Conditions of enrichment can be defined by the person skilled in the art depending on the chemistry of the particular molecule and the technique.

The elution step can be performed by using any techniques permitting to separate bound ligand moiety/anti-ligand molecule. These techniques are well described in literature and are based on physico-chemical properties of said binding. For example, it is possible to vary pH or ionic strength conditions. It is further possible to use eluting compound capable of competing with the specific binding of the ligand and the molecule.

Another object of the invention is a kit for detecting the anti-ligand molecule, or by extension any compound comprising such an anti-ligand molecule (e.g. tumoral cells), including the reagent described above, attached to a solid substrate that is compatible (i.e. does not prevent binding of the ligand moiety with anti-ligand molecule) with said reagent.

Finally, the poxviral particles according to the instant invention, may be identified by using the following process. First, a poxviral particle library is provided. Said poxviral particle library is designed for cloning random polypeptide ligand moieties and expressing them in the correct folding at the poxviral surface. As used herein, the term "library" means a collection of poxviral particles exhibiting at their surface a few or a large number of different ligand moieties, varying from about ten to several billions. Preferably, the ligand moiety is a single chain fragment of an antibody or a peptide. A poxviral particle library expressing diverse populations of ligands at the viral surface can be prepared as described for phage display library (WO97/10507) or vaccinia direct ligation vectors (Merchlinsky et al., 1997, Virol 238, 444-451). Alternatively, one may use nucleic acid sequences from expression libraries (genomic fragments, cDNA from selected organs and tissues) or random libraries expressing peptide motifs. Such librairies are described in the literature or commercially available (Invitrogene, USA reference K1125-01; Clontech Laboratories Inc reference NL4000AA).

Preferably, as described above, the nucleic acid sequence encoding the polypeptide ligand moiety is cloned into an appropriate poxviral gene encoding a protein naturally localized onto the surface of the poxviral particle. In a preferred embodiment, the polypeptide ligand moiety is expressed as a fusion protein with one of the IMV or EEV surface polypeptides. In a more preferred embodiment, the polypeptide ligand moiety is fused in frame at the N-terminus of either the p14 protein present onto the IMV surface or the B5R gene product present onto the EEV surface.

Then, said poxviral particle library is placed in contact with an immobilized reagent consisting in identified anti-ligand molecule, or by extension identified compound comprising such an anti-ligand molecule (e.g. tumoral cells expressing MUC1). The contact is made during a sufficient period of time to allow the specific binding of the ligand moiety present at the surface of the poxviral particles library with the identified anti-ligand molecule present in the immobilized reagent. Specific binding can be enhanced by appropriate pH and osmolarity conditions. Preferably, the poxviral particle library is placed in a buffering solution having a pH comprised between approximately 6 and approximately 9.5 and, more preferably, between approximately 7 and approximately 8.5. In addition, various methods can be useful for preventing non-specific binding, for example by performing a preadsoption step using a any agent useful for blocking non-specific binding (e.g. serum albumin, dextran sulfate and the like) prior to the contacting step.

The unbound particles are eliminated and the bound particles are eluted. Reagent immobilisation and elution conditions are performed as described above. The poxviral particles from the library which have been retained by binding on the immobilized reagent are then analyzed. More particularly, said analysis is carried out by sequence determination of the ligand moiety encoding nucleic acid inserted in the genome of the isolated poxviral particles. The binding specificity of the ligand moiety identified within this process can be easily confirmed (i) by using target cells and non target cells, and controlling infectious property of the poxviral particles presenting said ligand moiety in accordance with the methods disclosed in the Experimental section or (ii) by preparing a reagent according to the invention, immobilizing it onto a solid support and implementing a method for assaying target cells and non target cells as described above.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example, the public database "Medline" may be used which is available on Internet, e.g. under http://www.ncbi.nlm.nih.gov/PubMed/medline.html. Further databases and addresses, such as http://www.ncbi.nlm.nih.gov, http://www.infobiogen.fr, http://www.fmi.ch/biology/research_tools.html, http://www.tigr.org, are known to the person skilled in the art and can also be obtained using, e.g., http://www.lycos.com. An overview of patent information in biotechnology and a survey of relevant sources of patent information useful for retrospective searching and for current awareness is given in Berks, TIBTECH 12 (1994), 352-364.

The present invention also concerns a method for the purification of a poxviral particle of the invention from a viral preparation containing both the poxviral particle of the invention and a wild type poxviral particle, comprising the steps of binding said viral preparation to a solid support coated with an anti-ligand molecule capable of binding said heterologous ligand moiety and recovering said poxviral particle. Preferably, the binding step is performed by surface plasmon resonance, preferably using a BIAcore X™ biosensor system (BIAcore AB, Uppsala, Sweden) according to the instructions of the manufacturer. According to a preferred embodiment, steptavidine is covalently bound to the solid support of a SA sensor chip by amine coupling using the amine coupling kit (BIAcore AB, Uppsala, Sweden). Then, biotinylated anti-ligand molecule is immobilized in flow cell on the SA sensor chip coated with steptavidine. Flow cell 1 served as reference. Binding of fluid phase poxviral particles of the invention was determined over a range of $1\times10^4$-$1\times10^{10}$ pfu/ml. Injection volumes are comprised between 5 to 100 μl and flow rate comprised between 2 and 10μl/min. The surface is regenerated with NaOH (2 to 50 mM) for recovery of specific targeted particles. Preferably, the solid support is a dextran support. Preferably, the anti-ligand molecule is a MUC-1-derived peptide, and especially a 60 mer representing 3 tandem repeats of MUC-1.

The method of the invention further comprises the step of infecting a permissive cell with said recovered poxviral particle. This step is performed according to standard technology. Preferably, the infection step is performed in the presence of EDTA (0.1to 10 mM with a preference for 1 mM).

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced different from what is specifically described herein.

All of the above cited disclosures of patents, publications and database entries are specifically incorporated herein by reference in their entirety to the same extent as if each such individual patent, publication or entry were specifically and individually indicated to be incorporated by reference.

LEGENDS OF THE FIGURES

FIG. 1 illustrates the poxviral particle organization. The IMV envelope is represented with a fine line displaying at its surface the D8L gene product and the complex of p21-kDa (p21) and p14-kDa protein (p14). The EEV envelope is represented with a bold line displaying at its surface the A34R, HA and B5R gene products.

Figure 1:
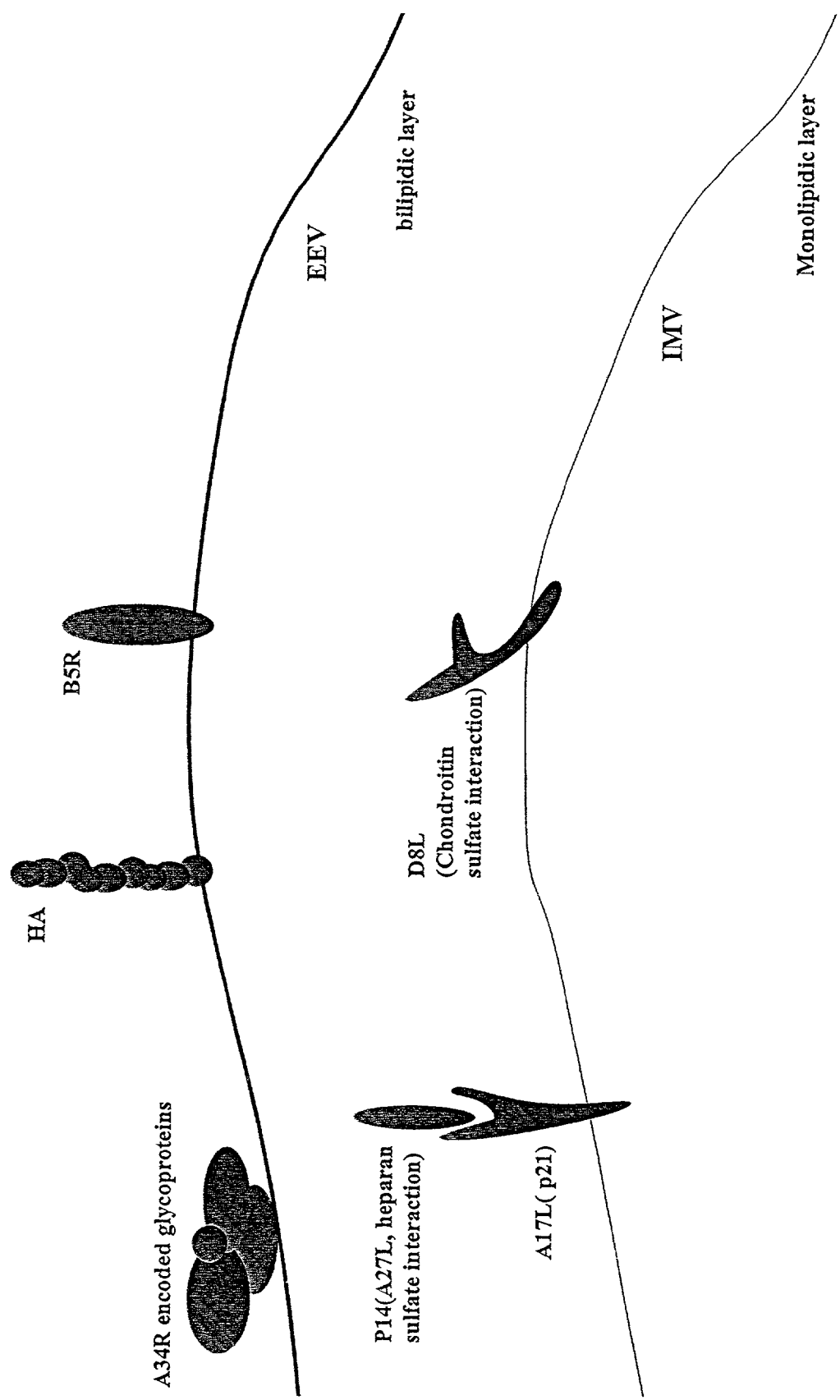

The following examples serve to illustrate the present invention.

EXAMPLES

The constructions described below are carried out according to the general genetic engineered and molecular cloning techniques detailed in Maniatis et al. (1989, Laboratory Manual, Cold Spring Harbor Laboratory Press, Cold Spring Harbor N.Y.) or according to the manufacturer's recommendations when a commercial kit is used. PCR amplification techniques are known to the person skilled in the art (see for example PCR protocols—A guide to methods and applications, 1990, published by Innis, Gelfand, Sninsky and White, Academic Press).

The recombinant M13 bacteriophages are growth on the E. coli NM522 strain (Stratagen) in an agar-based minimal medium or in a liquid rich LBM medium. The recombinant plasmids carrying the ampicillin resistance gene are replicated in the E. coli C600 (Stratagene), BJ5183 (Hanahan, 1983, J. Mol. Biol. 166, 557-580) and NM522 on agar or liquid medium supplemented with 100 µg/ml of antibiotic. The BJ5183 strain is preferably used when the cloning is carried out by homologous recombination (Bubek et al., 1993, Nucleic acid Res. 21, 3601-3602).

The constructions of the recombinant vaccinia viruses are performed according to the conventional technology in the field in the documents above cited and in Mackett et al. (1982, Proc. Natl. Acad. Sci. USA 79, 7415-7419) and Mackett et al. (1984, J. Virol. 49, 857-864). The selection gene gpt (xanthine guanine phosphoribosyltransferase) of E. Coli (Falkner and Moss, 1988, J. Virol. 62, 1849-1854) is used to faciliate the selection of the recombinant vaccinia viruses.

Example 1

Construction of a MVA Targeting MUC1 Positive Cells

Two Different Constructions have been Engineered:

MVATG14519 is a MVA vector engineered to target MUC-1 positive tumor-cells that expresses a chimeric p14 protein in which the scFv chain of SM3 monoclonal antibody is fused in its native form to the N-terminus of the MVA 138L ORF (p14-kDa).

MVATG14552 (FIG. 2) is a MVA vector engineered to target MUC-1 positive tumor-cells and which is similar to MVATG14519 vector with the exception of the presence of a signal peptide of the human trans-golgi network glycoprotein TGN51 (sequence described by Kain et al., 1997, J. Biol. Chem 273, 981-988) fused at the N-terminus of the scFv chain of SM3 monoclonal antibody.

A. MVA138L Gene Modification.

A cloning vector for the insertion of scFv sequences has been assembled using a PCR based strategy. The 3' end of MVA138L gene and 3' flanking region are amplified using the primers OTG12340 (SEQ ID NO: 1) and OTG12343 (SEQ ID NO: 2) to produce fragment C. The selection marker expression cassette coding for the E. Coli gpt placed under the control of the early-late promoter pH5R (Goebel et al., 1990, Virol 179, 247-266, 517-563) is isolated by PCR from a prior art plasmid DNA, such as pH5R-GPT (FR 98 13279) (designated hereinafter pTG9996), using the primers OTG12342 (SEQ ID NO: 3) and OTG12341 (SEQ ID NO: 4) to produce fragment E. The fusion between fragments C and E is performed by PCR by mixing both fragments and the primers OTG12340 and 12342 (Fragment F).

The upstream region of MVA138L is amplified with the tandem primer OTG12338 (SEQ ID NO: 5) and OTG12359 (SEQ ID NO: 6) in the case where the scFv is fused to the native p14-kDa to generate fragment A which is subsequently cloned between EcoRI and HindIII sites of M13TG6131 (Example 7 of WO99/03885) to give rise to M13TG14025. In the case where the scFv is fused at its N-terminus to the trans-golgi network glycoprotein TGN51 translocation signal, the amplification is performed with the primers OTG12338 (SEQ ID NO: 5) and OTG12346 (SEQ ID NO: 7). The resulting fragment (Fragment Asp) is cloned between EcoRI and HindIII sites of M13TG6131, to give M13TG14027. Both constructions include a unique HindIII site upstream the MVA138L coding sequence.

The MVA138L and the downstream region of MVA138L are amplified using the primers OTG12380 (SEQ ID NO: 8) and OTG12339 (SEQ ID NO: 9). The resulting fragment (fragment D) is cloned between EcoRI and HindIII sites of M13TG6131, to give M13TG14026. Fragments A/D or Asp/D are isolated by digestion with HindIII and EcoRI and inserted in the EcoRI site of the vector pTG1E (Example 2 of WO99/03885), to give respectively pTG14359 (containing the A/D fragment) and pTG14358 (containing the Asp/D fragment). Fragment F is then inserted either within pTG14359 or pTG14358 at the PacI site. Final constructs are named pTG14366 and pTG14365.

B. Isolation of SM3 scFv.

Figure 2:
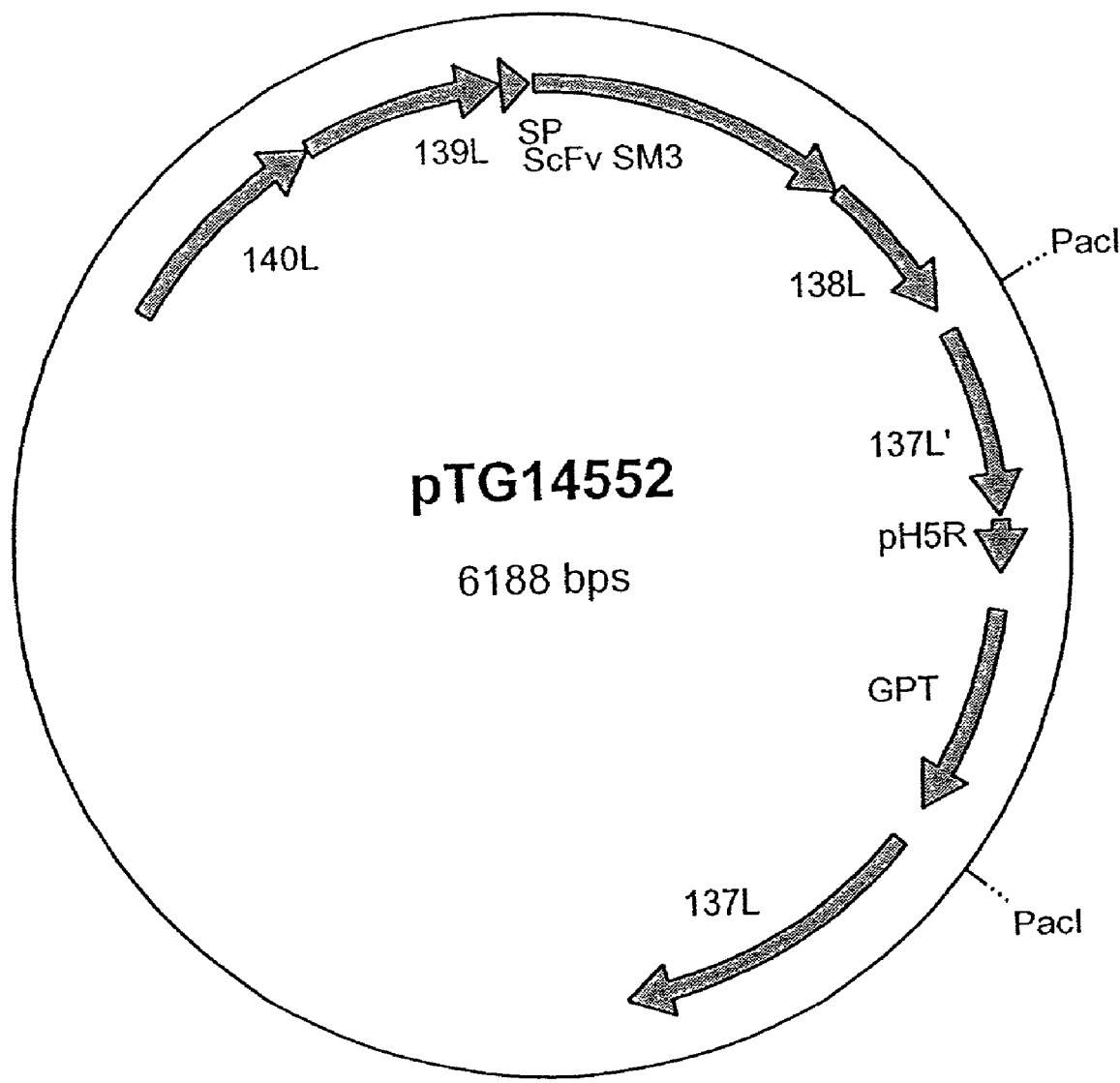
FIG. 2 represents schematically the plasmid pTG14552.

The SM3 hybridoma has been described by Burschell et al. (1987, Cancer Res 47, 5476-5482), Girling et al. (1989, Int J Cancer 43, 1072-1076) and Dokurno et al. (1998, J. Mol. Biol. 284, 713-728). The epitope recognized onto the MUC-1 tumor associated form is P-D-T-R-P. SM3 scFv comprises the variable region of the SM3 antibody heavy chain (referred within the GeneBank under the accession numbers AF042142) linked to a 10 residues spacer followed by the variable region of the SM3 antibody light chain (referred within the GeneBank under the accession numbers AF042143). Each variable region can be isolated by PCR from a prior art plasmid such as pMAL-SM3 using either the tandem primers OTG12360 (SEQ ID NO: 10) and OTG12361 (SEQ ID NO: 11) for the insertion of the SM3-scFv sequence within the HindIII site of pTG14366 or the tandem primers OTG12344 (SEQ ID NO: 12) and OTG12361 (SEQ ID NO: 11) for the insertion of the SM3-scFv sequence within the HindIII site of pTG14365. The resulting constructs are named pTG14519 and pTG14552 (FIG. 2).

C. Isolation of MVA Infectious Particles.

A subclone of MVA has been isolated in GMP conditions from a crude material as described in Stickl et al. (1974, Deutsch Med Wochenschr 99, 2386-2392; Mayr et al., 1978, Zentralbl Bakteriol 167, 375-390). This subcloned is named MVATGN33.1. This parental MVA is routinely propagated and tittered onto CEFs.

CEFs are prepared from chicken embryo obtained from fertilized eggs previously incubated 11 days at 37° C. in a humid atmosphere. Chicken embryo are cut up into small pieces and treated with a solution of trypsin 2.5% (w/v). CEF are then plated onto Falcon 3001 plastic Petri dishes at a cell density of $1.5 \times 10^6$ cells/dish in Eagle Based Medium (MBE)/tryptose (Gibco BRL) complemented with 10% calf serum. After 48 h, monolayer cells are infected with the MVATGN33.1 for 30 min in PBS plus cations (magnesium acetate and $CaCl_2$ 1 mg/ml each) plus 1% calf serum in order to adsorb the virus onto the cells. Infected cells are then cultivated for one hour in MBE plus 5% calf serum at 37° C. 5% $CO_2$. 1 to 5 g of plasmid (pTG14519 or pTG14552) are then precipitated in a solution of Hepes and $CaCl_2$. The precipitated DNA is layered onto the infected cell monolayer and incubated 2 h at 37° C. and 5% $CO_2$. A glycerol shock can be performed during 1 minute in order to facilitate the plasmid entry. For this purpose, a solution of 10% of glycerol in MBE/Tryptose is layered onto the cell monolayer for 1 min. Monolayers are then washed with PBS plus cations and incubated in MBE plus 5% of calf serum at 37° C. and 5% $CO_2$. After 48 h the Petri dishes are frozen.

The isolation of recombinant plaques is performed as follows: the Petri dishes are thawed, the infected cells are harvested and sonicated within the MBE/Calf serum. Recombinant viruses are then isolated by consecutive rounds of plaque purification in CEFs under the pression of the selection marker in the presence of 250 µg/ml of xanthin, 15 µg/ml of hypoxanthin, and 25 µg of mycophenolic acid as previously described by Falkner and Moss (1988, J. Virol. 62, 1849-1854).

A stock (viral seed) can be prepared in F175 flasks containing $10^8$ CEFs that are infected with the MVA. Viruses are propagated for 48 to 72 hours. The infected cells and the culture medium are pooled and the suspension is sonicated. Crude extracts are first fractionated onto a 36% sucrose cushion. Viral pellet is then fractionated onto a discontinuous sucrose gradient, as described in Joklik (1962, Virology 18, 9-18).

Example 2

Construction of a Recombinant MVA Expressing FCU-1 and Targeting MUC1 Positive Cells FCU-1 gene was isolated by HindIII/KpnI digestion of the DNA plasmid pTG13046 (referred as pCI-neoFCU1 in WO99/54481). The transfer vector containing the homologous sequences to the flanking regions of the deletion III named pTG6019 (Example 2 of WO99/03885) was modified as follow. The expression cassette coding for E. coli gpt placed under the control of the early late pH5R vaccinia virus promoter is isolated from the DNA plasmid pTG9996 by a SacI digestion. This DNA fragment is then inserted within the SacI site of the DNA plasmid pTG6019, to give pTGI4033. The synthetic early late promoter p11K75 (SEQ ID NO: 13) is isolated by PCR from the template M13TG4052 with the primers OTG122271 (SEQ ID NO: 14) and OTG12272 (SEQ ID NO: 15). M13TG4052 is based on M13TG130 (Kieny et al. 1983, Gene 26, 91-99). The promoter 11K7.5 contains from 5' to 3' the sequence of the late promoter 11 k (Goebel et al., 1990, supra) up to nucleotide +4 of the transcription initiation site, the sequence of the TK promoter from nucleotides −28 to −13 having a C instead of a A at position −18 and the region between nucleotides −12 to +6 of the early 7.5 k promoter.

The amplified fragment is digested by BamHI and BglII restriction enzymes before being inserted within the BamHI site of pTG14033, to give pTG14084. The FCU-1 gene is cloned downstream the p11K75 promote by homologous recombination as follows. First, synthetic sequences are inserted between the PstI and BamHI sites of pTG14084 using OTG12522 (SEQ ID NO: 16) and OTG12523 (SEQ ID NO: 17). The DNA plasmid is then linearized by XhoI and homologous recombination with the FCU-1 gene is performed in E. coli. The resulting DNA plasmid is named pTG14322.

Homologous recombination in CEFs infected with MVATG14552 and transfected with pTG14322 results in the obtention of a MUC1 targeted MVA expressing the suicide gene FCU-1.

Example 3

Production of MVA with a Knockout of F13L Gene

The 5' F13L flanking region is isolated from MVATGN33 viral DNA by standard PCR assay using the tandem primers OTG13192 (SEQ ID NO: 18) and OTG13194 (SEQ ID NO: 19) and inserted between the BamHI and EcoRI sites of pBS (Stratagene) (pTG14746). The 3' F13L flanking region is isolated from MVATGN33 viral DNA by standard PCR assay using the tandem primers OTG13190 (SEQ ID NO: 20) and OTG13191 (SEQ ID NO: 21) and inserted between the BamHI and EcoRI sites of M13TG6131 to give M13TG14101. 5' and 3' F13L flanking regions are then cloned in the EcoRI site of pTG1E. The resulting construct is named pTG14783.

Example 4

Generation of a Producer Cell Line Expressing for the MUC-1 Antigen

As mentioned above, insertion of the SM3 scFv ligand moiety in the p14-kDa protein may affect virus production (reduced virus yield). Thus, targeted MVA of Example 1 are preferably isolated and propagated on a cell line exhibiting at the cell surface the MUC-1 antigen which is recognized by the SM3 antibody present at the viral surface, in order to reduce contamination with the wild type MVATGN33.1.

The cDNA encoding the membrane anchored form of MUC-1 antigen is isolated from pPOLYII-ETAtm (Hareuveni et al., 1990, Eur. J. Biochem 189, 475-486) by a double digestion with BglII and EcoRI restriction enzymes and inserted between the BamHI and EcoRI sites of the pcDNA3 expression vector (InVitrogen, USA) downstream the CMV promoter. The resulting plasmid is named pTG5077.

$1 \times 10^6$ BHK-21 (ATCC CCL-10) cells are transfected with 5 µg of pTG5077 and subsequently cultured in GMEM (Glasgow Modified Eagle Medium, Gibco BRL) containing 20 g/l of Gentamycin and 10% fetal calf serum. After 24 h at 37° C. in 5% CO2 atmosphere, 1 mg/ml of G418 (Gibco BRL) is added. Neomycin resistant clones are then isolated by limit dilution and tested by FACS for MUC-1 expression at the cell surface using the H23 monoclonal antibody (Tsarfaty et al., 1989, in Breast cancer immunodiagnosis and Immunotherapy, Ed Ceriani, Plenum NY). Interestingly, most of the MUC-1 positive clones loose the plastic adherence property of the parental BHK-21 cell line and start to grow in suspension. This observation will facilitate propagation and pharmaceutical production of the recombinant viruses of the invention in bioreactor.

Example 5

Evaluation of the Targeting Properties

Clones of MVATG14552 of Example 1 are isolated by consecutive rounds of plaque purification in CEFs under selective condition in the presence of xanthin, hypoxanthin and mycophenolic acid as described above.

A certain number of clones are first analyzed by PCR to detect the presence in the viral genome of the chimeric gene encoding the TG51/SM3scFv/p14kDa fusion protein. Nine clones are selected and further analyzed by Western Blot to confirm the expression of the fusion protein at the surface of the poxviral particles. Detection is performed with the ECL kit (Amersham) by immunoblotting with a p14-kDa specific rabbit polyclonal serum in crude extract obtained from infected cells or supernatants. Purified p14-kDa protein is used as a control. With the exception of clone C5, all the selected clones express the chimeric fusion protein that has a molecular mass of 46 kDa. As expected, the intensity of the labeling is more intense in crude extracts than in culture supernatants reflecting the intracellular status of the poxviral particles. These results indicate that the majority of the poxviral exhibiting at their surface the TG51/SM3scFv/p14kDa fusion protein are IMV particles. The detection of weak amount of fusion protein in the culture supernatant can be explained either by a breakage of the EEV envelope or by a cellular lysis during clone preparation.

Infection properties of MVATG14552 have then be studied in different cell lines:

The murine mastocytoma P815 (ATCC CRL6448),

P815 expressing the MUC-1 antigen (P815-MUC1) obtained by transfection of the parental P815 cells with a vector expressing the membrane anchored form of MUC1 antigen, BHK 21 (Baby Hamster Kidney), BHK 21 expressing the MUC-1 antigen (BHK 21-MUC1) obtained by transfection of the parental BHK 21 cells with a vector expressing the membrane anchored form of MUC1 antigen.

Figure 3:
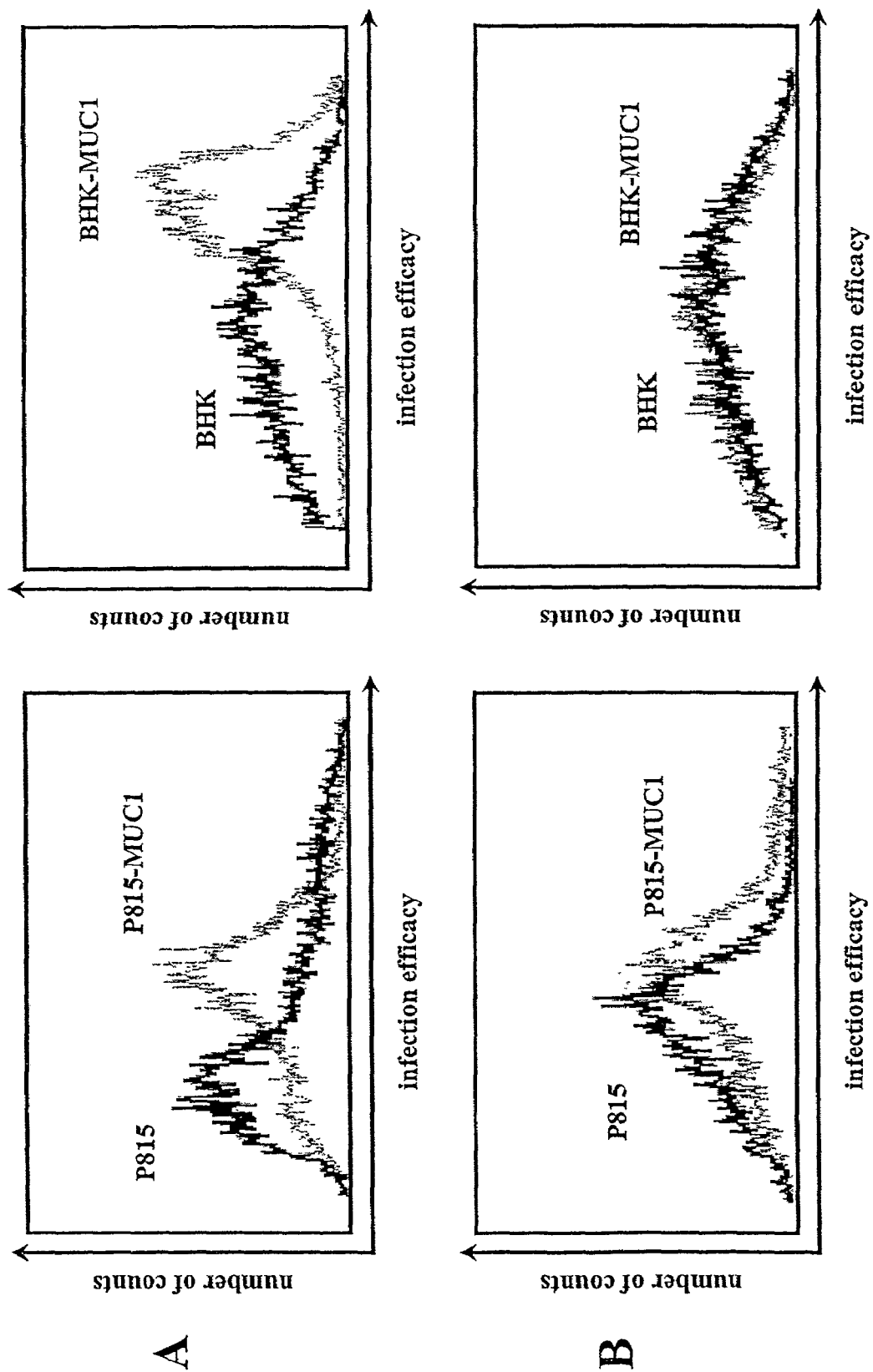
FIG. 3 represents a flow cytometry analysis following infection of P815, MUC-1 expressing P815 (P815-MUC1), BHK-21 and MUC-1 expressing BHK-21 (BHK-21-MUC1) by MVATG14552 (A) or the control MVAN33 (B).

Cells are infected with MVATG14552 clone 9 or with a control virus (MVAN33) at a MOI of approximately 0.1 for 24 h. Infection efficiency is determined by flow cytometry (FACS) after incubation with a polyclonal murine serum obtained after MVA immunization at a dilution rate of 1/100. Revelation is made by incubation with a monoclonal FITC goat anti-mouse IgG (Pharmingen, 10 µg/ml). As shown in FIG. 3A, MVATG14552 infects preferably MUC-1 expressing cells compared to the parental cells P815 and BHK-21. On the contrary, the control MVA infects both the MUC-1 expressing and non expressing cells with a similar efficiency (FIG. 3B).

All together, these results indicate that the ligand moiety SM3 scFv is expressed at the surface of the poxviral (IMV) particles and that it is capable of recognizing and binding to its target (the MUC-1 antigen) leading to a specific infection of said cells by the modified virus.

The interactions between two SM3 scFv expressing clones (A3 and C9) with a MUC-1 60 mer peptide were examined by Surface Plasmon Resonance (SPR), using a BIAcore XTM biosensor system (BIAcore AB, Uppsala, Sweden). All experiments were performed at 25° C. Steptavidine was covalently bound to the carboxylated dextran matrix of a SA sensor chip by amine coupling using the amine coupling kit (BIAcore AB, Uppsala, Sweden). Then, biotinylated 60 mer peptide representing 3 tandem repeats of MUC-1 (10 µg/ml in HBSS buffer) was immobilized in flow cell 2 on the SA sensor chip coated with steptavidine. Flow cell 1 served as reference. Binding of fluid phase recombinant SM3 was used as positive control. Binding of fluid phase recombinant viruses was determined over a range of $1 \times 10^6$-$1 \times 10^8$ pfu/ml in HBSS buffer. For this purpose, primary chicken fibroblasts were infected at a MOI of 1 during 24 h with the viral suspensions. Injection volumes were 15 µl and flow rate 5 µl/min. The surface was regenerated with 10 mM NaOH. Kinetic analysis was performed using a BIAevaluation 3.0 software. A specific and reproductible interaction between recombinant viruses and the 60 mer MUC-1 peptide was observed. The measurements were found to correlate with virus concentrations. Binding of control MVA (MVAN33) to the same peptide was never observed.

These results demonstrate that the SM3 scFv/p14 fusion protein associates with MVA particles and that the recombinant viruses recognize specifically a MUC-1-derived peptide.

Example 6

Purification of the SM3 scFv-Expressing Viral Particles

In order to separate the non-recombinant wild type viral particles from the recombinant ones, a selection protocol was performed by the BIAcore technique to purify the recombinant SM3 scFv-expressing viral particles based on their capability of binding a MUC-1 peptide. A viral preparation made from clone A3 was injected in the BIAcore X system as described above. The viruses displaying a high affinity for the 60 mer MUC-1 peptide were recovered at the surface during the regeneration phase using 20 mM NaOH, as described in BIAcore X Instrument Handbook. Permissive cells were then infected with the recovered viruses, in the presence of EDTA (1 mM) to avoid the formation of viral aggregates and the recombinant viruses were selected by a double selection GUS/GPT. The absence of wild type non recombinant viruses was assessed in isolated clones by PCR. This new purification and selection protocol has allowed the obtention of several clones free of contaminating wild type viruses.

The invention claimed is:

1. An intracellular mature virus (IMV) vaccinia virus particle having a targeted infection specificity towards target cells, wherein:
   said IMV vaccinia virus particle infects said target cells;
   said targeted infection specificity is conferred by the binding of at least one ligand moiety localized at the surface of said IMV vaccinia virus particle to an anti-ligand molecule localized at the surface of said target cells;
   said at least one ligand moiety comprises an antibody fragment or a binding moiety of a normal cell surface receptor;
   said antibody fragment or binding moiety of a normal cell surface receptor is fused to the N-terminus of the expression product of the vaccinia virus A27L gene so as to produce a chimeric polypeptide localized at the surface of said IMV vaccinia virus particle;
   said anti-ligand molecule is selected from the group consisting of: a cell-specific marker, a tissue specific marker, a viral antigen, and a tumor-associated marker; and
   said IMV vaccinia virus is selected from the group consisting of Copenhagen, Wyeth and Ankara modified (MVA) strains.

2. The IMV vaccinia virus particle of claim 1, wherein: said target cells are tumoral cells; and said anti-ligand molecule is a tumor-associated marker.

3. The IMV vaccina virus particle of claim 1, wherein said ligand moiety comprises an antibody fragment that recognizes and binds to the MUC-1 antigen.

4. The IMV vaccina virus particle of claim 3, wherein said antibody fragment is the scFv fragment of the SM3 monoclonal antibody.

5. The IMV vaccinia virus particle of claim 1, wherein said ligand moiety further comprises a signal peptide that facilitates the insertion of said ligand moiety into the envelope of said IMV vaccina virus particle.

6. The IMV vaccina virus particle of claim 5, wherein said signal peptide further facilitates the translocation of said ligand moiety into the trans-Golgi network.

7. The IMV vaccina virus particle of claim 6, wherein said signal peptide is a signal peptide of the human trans-Golgi network glycoprotein TGN51.

8. The IMV vaccina virus particle of claim 1, wherein said IMV vaccina virus particle further comprises a nucleic acid of interest.

9. The IMV vaccina virus particle of claim 8, wherein said nucleic acid of interest is a suicide gene.

10. A composition comprising at least one IMV vaccina virus particle of claim 1 and a pharmaceutically acceptable vehicle.

11. The IMV vaccina virus particle of claim 1, wherein at least a portion of the expression product of the vaccinia virus A27L gene is removed and replaced by said ligand moiety.

12. The IMV vaccina virus particle of claim 1, wherein said ligand moiety is incorporated into the expression product of the vaccinia virus A27L gene.

13. The IMV vaccina virus particle of claim 1, wherein said anti-ligand molecule is overexpressed in said target cells or is a gene product of a cancer-associated virus.

14. The IMV vaccinia virus particle of claim 2, wherein said tumor-associated marker is selected from the group consisting of: a receptor for interleukin 2 (IL-2), a GRP (Gastrin Release Peptide), a TNF (Tumor Necrosis Factor) receptor, an epidermal growth factor receptor, a Fas receptor, a CD40 receptor, a CD30 receptor, a CD27 receptor, an OX-40, a Vv integrin, an angiogenic growth factor receptor, and a gene product of a cancer-associated virus.

* * * * *

UNITED STATES PATENT AND TRADEMARK OFFICE
CERTIFICATE OF CORRECTION

PATENT NO. : 7,354,591 B2 Page 1 of 1
APPLICATION NO. : 09/832899
DATED : April 8, 2008
INVENTOR(S) : Jean-Marc Balloul et al.

It is certified that error appears in the above-identified patent and that said Letters Patent is hereby corrected as shown below:

On the title page:
Item 60 (Related U.S. Application Data): change Provisional application "60/256,080, filed on Dec. 15, 2000" to --60/246,080, filed Nov. 7, 2000--.

Signed and Sealed this

Eighth Day of July, 2008

JON W. DUDAS
*Director of the United States Patent and Trademark Office*